(12) United States Patent
Hennink et al.

(10) Patent No.: US 7,776,359 B1
(45) Date of Patent: *Aug. 17, 2010

(54) STEREOCOMPLEX HYDROGELS

(75) Inventors: Wilhelmus Everhardus Hennink, Waddinxveen (NL); Cornelis Franciscus van Nostrum, Nuenen (NL); Silvia Johanna de Jong, De Maern (NL)

(73) Assignee: Universiteit Utrecht, Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/913,967

(22) PCT Filed: Feb. 21, 2000

(86) PCT No.: PCT/NL00/00108

§ 371 (c)(1),
(2), (4) Date: Dec. 31, 2001

(87) PCT Pub. No.: WO00/48576

PCT Pub. Date: Aug. 24, 2000

(30) Foreign Application Priority Data

Feb. 19, 1999 (EP) .................................. 99200472

(51) Int. Cl.
*A61K 9/14* (2006.01)
*A61F 2/00* (2006.01)
(52) U.S. Cl. ........................ 424/486; 424/426; 424/488; 424/489

(58) Field of Classification Search .................. 424/486, 424/484, 426, 488, 489
See application file for complete search history.

(56) References Cited

U.S. PATENT DOCUMENTS

| 4,526,938 A | 7/1985 | Churchill |
| 4,650,488 A * | 3/1987 | Bays et al. ................ 623/23.64 |

(Continued)

FOREIGN PATENT DOCUMENTS

| JP | 58-191714 | 11/1983 |
| JP | 61-036321 | 2/1986 |

(Continued)

OTHER PUBLICATIONS

Okihara et al., J. Macromol. Sci. Phys. (1991) B30 (1 & 2): 119-140.*

(Continued)

*Primary Examiner*—Blessing M Fubara
(74) *Attorney, Agent, or Firm*—Morrison & Foerster LLP

(57) ABSTRACT

The invention relates to hydrogel compositions, which can be applied as biodegradable materials and to the processes to prepare such hydrogels. The hydrogel of the present invention comprises a stereocomplex gel structure which is the result of the interaction of oligomerized monomers of one chirality with that of oligomerized monomers of the opposite chirality, both grafted to hydrophilic polymers. The grafts form an interaction which is different from a covalent chemical interaction and thus provide the gel with the required coherence.

10 Claims, 11 Drawing Sheets

U.S. PATENT DOCUMENTS

Figure 1:
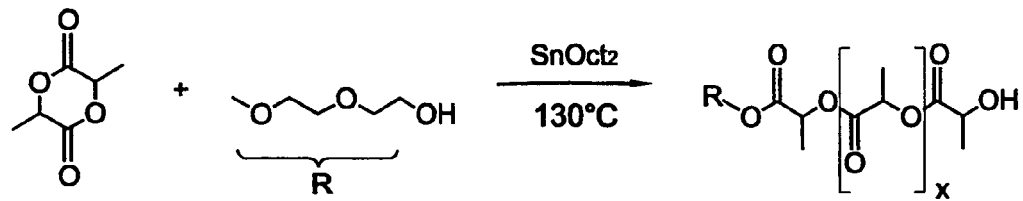
Figure 1:
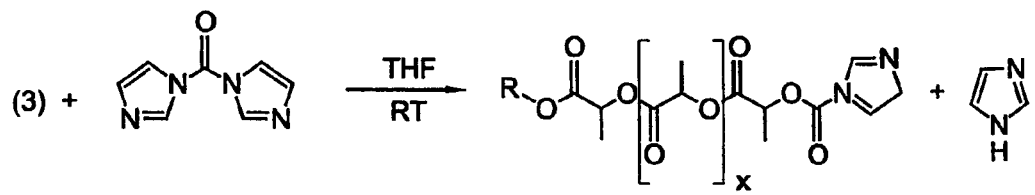
Figure 1:
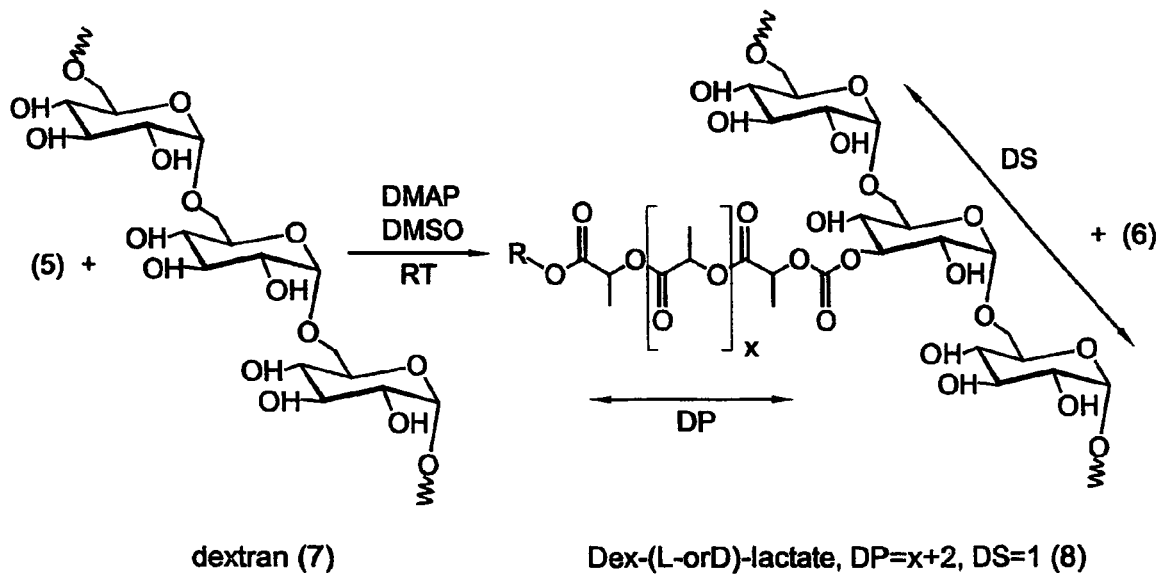

| | | | | | |
|---|---|---|---|---|---|
| 4,788,979 | A | * | 12/1988 | Jarrett et al. | 606/230 |
| 4,814,182 | A | * | 3/1989 | Graham et al. | 424/484 |
| 4,902,515 | A | | 2/1990 | Loomis et al. | |
| 5,230,900 | A | * | 7/1993 | Hakomori et al. | 424/450 |
| 7,049,357 | B2 | * | 5/2006 | Craun et al. | 524/284 |

FOREIGN PATENT DOCUMENTS

| | | | |
|---|---|---|---|
| JP | 04-210928 | | 8/1992 |
| JP | 11-269097 | | 10/1999 |
| JP | 2000-017163 | | 1/2000 |
| JP | 2000-515853 | | 11/2000 |
| WO | WO 98/00170 | | 1/1998 |
| WO | WO 9800170 | * | 1/1998 |
| WO | WO 99/36100 | | 7/1999 |

OTHER PUBLICATIONS

De Jong et al., Macromoleculesn(1998) 31: 6397-6402.*
Brannon-Peppas, Int. J. Pharm. (1995) 116: 1-9.*
Okihara et al., J. Macromol. Sci. Phys. (1991) 830 (1 & 2): 1 19-140.*
De Jong et al., Macromoleculesntlgg8) 31: 6397-6402.*
Brannon-peppas, Int. J. Pharm. (1995) 1 16: 1-9.*
De Jong et al., Macromolecules, 31(19):Sep. 22, 1998 31:6397-6402.*
Y. Li, J. Nothnagel and T. Kissel, Biodegradable brush-like polymers from poly(D,L-lactide) or poly(D,L-lactide-co-glycolide) and charge-modified, hydrophilic dextrans as backbone—synthesis, characterization and in vitro degradation properties. Polymer 38 (1997), pp. 6197-6206.*
Y. Li, C. Volland and T. Kissel, Biodegradable brush-like polymers from poly(D,L -lactide) or poly(D,L,-lactide-co-glycolide) and charge-modified, hydrophilic dextrans as backbone—in vitro degradation and controlled release of hydrophilic release of hydrophilic macromolecules. Polymer 39 (1998), pp. 3087-3097.*
Bot et al., Polymer Gels and Networks (1996) 4:189-227.
Brannon-Peppas, Int. J. Pharm. (1995) 116:1-9.
Chemical Abstracts, Database Accession No. 132:180789 (XP-002141115), Jul. 1999.
De Jong et al., Macromolecules (1998) 31:6397-6402.
De Jong et al., Macromolecules (2000) 33:3680-3686.
De Smedt et al., Micromolecules (1995) 28:5062-5088.
Evens and Sindelar, Biotechnology Products in the Pipeline, in: Pharmaceutical Biotechnology, Crommelin and Sindelar (eds.), Harwood Academic Publishers (1997) pp. 337-355.
Kister et al., Polymer (1995) 39:267-273.
Okihara et al., J. Macromol. Sci. Phys. (1991) B30(1&2):119-140.
Park et al. (eds), Biodegradable Hydrogels for Drug Delivery, Technomic Publishing Co. Inc. (1993) p. 75.
Smith et al., Anal. Biochem. (1985) 150:76-85.
Soeterboek and Verheggen, Pharm. Weekblad (1995) 130:670-675.
Van Dijk-Wolthuis et al., Macromolecules (1995) 28:6317-6322.
Van Dijk-Wolthuis et al., Macromolecules (1997) 30:3411-3413.
Elisseeff et al., Macromolecules (1997) 30:2182-2184.
Huh et al., Drug Delivery Tech. (2003) 3:4249.
Translation of Notification of Reason for Refusal for JP 2000-599368, mailed Nov. 10, 2009.

* cited by examiner

L-(or D-)lactide (1)   2(2-methoxyethoxy)ethanol (2)   L-(or D-)lactic acid oligomer (3)

CDI (4)   (L-orD)lactate-CI (5)   imidazole (6)

dextran (7)   Dex-(L-orD)-lactate, DP=x+2, DS=1 (8)

STEREOCOMPLEX HYDROGELS

This application is a 371 of PCT/NL00/00108 filed Feb. 21, 2000

The present invention relates to hydrogel compositions comprised of mixtures of water soluble or water dispersible polymers in an aqueous system, at least part of which polymers contain at least two groups, which groups can give an interaction. Furthermore, the present invention relates to processes for preparing such hydrogels, and the use of oligomeric or co-oligomeric groups on polymers for gel formation.

The fast developments in the field of molecular biology and biotechnology have made it possible to produce a large number of pharmaceutically interesting products in large quantities. For instance, pharmaceutically active peptides and proteins can suitably be used as drugs in the treatment of life-threatening diseases, e.g. cancer, and of several types of viral, bacterial and parasital diseases; in the treatment of e.g. diabetes; in vaccines, e.g. for prophylactic aims, and for anticonception purposes. Especially the specialized biological activities of these types of drugs provide tremendous advantages over other types of pharmaceutics.

To illustrate the fast developments, it has been reported (see e.g. Soeterboek and Verheggen, Pharm. Weekblad 130, pp. 670-675 (1995); R. P. Evens and R. D. Sindelar, 'Biotechnology products in the pipeline', In: Pharmaceutical Biotechnology (D. J. A. Crommelin and R. D. Sindelar, eds.), Harword Academic Publishers, pp. 337-355 (1997)) that in the United States of America, about 275 biotechnological products are in phase IV studies, while more than 500 products are under investigation.

Examples of (recombinant) proteins, which are considered very interesting from a pharmacological point of view, are cytokines, such as interleukines, interferons, tumor necrosis factor (TNF), insulin, proteins for use in vaccines, and growth hormones.

Due to their nature, proteins and proteinaceous products, including peptides, which group of products will be referred to as protein drugs herein-below, cannot be administered orally, at least not effectively. These products tend to degrade rapidly in the gastro-intestinal tract, in particular because of the acidic environment and the presence of proteolytic enzymes therein.

Moreover, to a high extent protein drugs are not able to pass endothelial and epithelial barriers, due to their size and, generally, polar character.

For these reasons, protein drugs have to be brought in the system parenterally, i.e. by injection. The pharmacokinetical profile of these products is, however, such that injection of the product per se requires a frequent administration. For, it is a known fact that proteinaceous material is eliminated from the blood circulation within minutes.

In other words, since protein drugs are chemically and/or physically unstable and generally have a short half-life in the human or animal body, multiple daily injections or continuous infusions are required for the protein drug to have a desired therapeutic effect. It will be evident that this is inconvenient for patients requiring these protein drugs. Furthermore, this type of application often requires hospitabilization and has logistic drawbacks.

In addition, it appears that at least for certain classes of pharmaceutical proteins, such as cytokines which are presently used in e.g. cancer treatments, the therapeutic efficacy is strongly dependent on effective delivery, e.g. intra- or peritumoral. In such cases, the protein drugs should be directed to the sites where their activity is needed during a prolonged period of time.

Hence, there is a need for delivery systems which have the capacity for controlled release. In the art, delivery systems consisting of a matrix of biodegradable polymers, (e.g. poly (DL-lactide-co-glycolide), see for example: J. L. Cleland, 'Protein delivery from biodegradable microspheres', in: Protein Delivery, Physical Systems, Pharmaceutical Biotechnology, Vol. 10, (L. M. Sanders and R. W. Hendren, eds.), Plenum Press, pp. 1-39 (1997) or L. Brannon-Peppas, 'Recent advances on the use of biodegradable microparticles and nanoparticles in controlled drug delivery', Int. J. Pharm., 116, pp. 1-9 (1995)) in which matrix proteins are present and from which they are gradually released, have been proposed.

Delivery systems can be obtained by using such biodegradable polymers for example in microspheres. However, in vitro or in vivo application of such systems based on poly(lactic acid) or poly(lactic-co-glycolic acid) have some inherent drawbacks. First, organic solvents have to be used to encapsulate proteins in the microspheres. Second, acidic products are formed during degradation, which might result in a lowering of the pH. Both a low pH and organic solvents can affect protein stability. Furthermore, it appears to be difficult to control the protein release from these systems, which can lead to a burst release.

A hydrogel system consisting of biodegradable polymers would overcome such objections. Hydrogels can be obtained by crosslinking of hydrophilic polymers. Crosslinking can be established by using aggressive and toxic cross-linking agents which are not compatible with proteins, such as bisfunctional agents, e.g., glutaraldehyde, diisocyanates and epichlorohydrin (See: Biodegradable hydrogels for drug delivery (K. Park, W. S. W. Shalaby and H. Park, eds.) Technomic Publishing Co. Inc., p. 75 (1993)). These are toxic compounds which have to be extracted from the gels before these gels can be therapeutically applied. Moreover, these compounds can also react with e.g. epsilon amine residues or lysine side chains of the protein that is present in the hydrogel matrix. This is highly unwanted because these reactions might result in loss or reduction of biological activity of the protein.

PCT/NL97/00374 describes a delivery system that provides one solution for this problem that improves the degradation properties. The hydrogel described in said PCT application is based on biodegradable polymers. More in particular, chains of these biodegradable polymers are intermolecularly crosslinked through linking groups, and these linking groups that keep the hydrogel together, are hydrolysable under physiological conditions, which effects the degradation of the hydrogel.

Although these hydrolysable hydrogels provide a gel with enhanced release properties, some disadvantages remain. The polymerization of dextran (-derivatives), for example, requires peroxydisulfate and TEMED as initiator/accelerator, which compounds are essentially incompatible with in vivo application. Furthermore, the use of an initiator may give rise to oxidation of proteins to sulfoxides. Therefore, it is required that these compounds are carefully removed.

It is the object of the present invention to provide a release delivery system that consists of a biodegradable hydrogel that can be applied in vitro and in vivo as a release system, wherein the crosslinks are not of a chemical nature, in the sense that the crosslinks are not covalent bonds. Consequently, such crosslinks do not require cleavage of chemical bonds.

To obtain a hydrogel composition that meets the demands set out in the above, several ways to modify polymeric chains have been investigated, and the present inventors have now found that when a hydrophilic polymer is substituted with grafts that contain elements with chiral differences, in particular elements that are enantiomers, a gel, i.e., a crosslinked structure, is obtained that has excellent properties, for the application as a release system, and in particular a controlled release system, for example for protein drugs.

Without wishing to be limited to a certain theory, the formation of this gelled structure is believed to be caused by the interaction of the grafts, which is believed to be similar to the interaction between the constituents of so called stereo-complexes. These stereocomplexes are racemic crystallites that are known to be formed from racemic mixtures of certain polymers. For example, it has been found (see, e.g., De Jong et al., Macromolecules, 31, pp. 6397-6402, (1998)) that the melting temperature of stereocomplexes of poly(lactic acid) is considerably higher than the melting temperature of both the enantiomer crystallites.

According to the present invention, the stereocomplex gel structure is the result of the interaction of oligomerized monomers of one chirality with that of oligomerized monomers of the opposite chirality, which oligomerized monomers are both present on hydrophilic polymers. The groups of oligomerized monomers can be present anywhere on the polymer chains, viz. also on the head or tail positions of the polymer chains. Preferably however, the groups of oligomerized monomers are present as branches or grafts on different polymer chains that constitute the gel structure. For clarity's sake it is noted that in the present description and claims, the term "graft" does not encompass oligomerized comonomers at the head and tail of a polymer backbone nor blocks of such oligomerized comonomers incorporated in a polymer backbone.

The gel is formed by mixing at least two different systems (A) and (B), each system being a solution or a dispersion of water soluble or water dispersible polymers, which polymers have oligomeric grafts. The grafts are obtained by polymerization of preferably one type of chiral monomer (e.g., D or L lactic acid).

The hydrogel composition according to the present invention is thus comprised of a mixture of (A) a water soluble or water dispersible polymer in an aqueous system at least part of which polymer contains at least two groups, which groups are oligomers or co-oligomers at least partly formed from chiral monomers, and (B) a water soluble or water dispersible polymer in an aqueous system at least part of which polymer contains at least two groups, which groups are oligomers or co-oligomers which are at least partly formed from chiral monomers with a chirality that is opposite to that of said monomers in mixture (A), such that the chiral part of the oligomers or co-oligomers in mixture (B) are in essence complementary to that of said groups of mixture (A); in which hydrogel composition the groups on the polymers from mixture (A) give a physical interaction with the groups from mixture (B).

System (A) comprises water soluble or water dispersible polymers with grafts formed from monomers of a certain chirality. System (B) comprises water soluble or water dispersible polymers with groups formed from monomers of an opposite chirality, viz. the enantiomers of the monomers used in system A.

Optionally, a small mole percentage of another monomer (e.g. glycolic acid) randomly placed in the group of oligomerized monomers is present. The presence of this comonomer should not prevent the ability of the groups, e.g. graft to give an interaction to form an associated complex with groups, e.g. grafts of the opposite chirality.

Alternatively, the graft is a co-oligomer that comprises a block-like structure, such as X—Y, in which X is formed from non-chiral monomers (e.g. a polyethylene glycol block) and Y is formed from chiral monomers (e.g. a poly(D or L lactic acid)block).

According to the present invention, a hydrogel can be obtained by mixing two or more water soluble or water dispersible polymers of the invention, which hydrogel has excellent release characteristics, is easily loaded with e.g. protein material, and that can be prepared without the use of organic solvents.

Preferably the oligomerized monomers, which are referred to as "grafts" herein-below are biodegradable. The grafts are preferably coupled to the polymer through hydrolysable bindings. The entire release system can be biodegradable or biocompatible.

It is also possible to obtain the desired effect, viz. the stereocomplex interaction, when grafts formed of monomers of one chirality and grafts formed of monomers of an opposite chirality are present on the same polymer chain. When such grafted polymers are present in the mixture, they are also able to display the stereocomplex interaction. Preferably, however, each polymeric chain is grafted with oligomers formed from monomers of the same chirality. More preferably, the grafts have a monodispersed distribution of the chain length, i.e., all grafts have essentially the same length.

It will be understood from the above that the characteristics of the formed gel will be determined to a great extent by the type, the number and the length of the grafts applied.

In the hydrogel according to the present invention, the average chain length of the oligomeric or co-oligomeric groups is preferably sufficiently low to render the polymer soluble or dispersible in water.

The hydrogel according the present invention comprises water soluble or water dispersible polymers in which the average chain length of the graft groups is preferably sufficiently high to obtain physical interaction between the grafts formed from monomers of opposite chirality, which physical interaction is different from the physical interaction that occurs when the grafts were formed from a racemic mixture of the same monomers.

Different amounts of enantiomers can be applied in one graft. It will be understood that the interaction between the grafts will be highest when the grafts on the polymer in one system is formed by monomers of one chirality, while the other portion of the grafts has an opposite chirality. Alternatively, it is also possible to use grafts that are enriched in monomers having one chirality instead of being exclusively formed by monomers of one chirality, as long as the grafts of the polymer in the other system is enriched in a fashion that it is in essence complementary to that of the first. This can be realized by e.g. oligomers or co-oligomers in the form of blocks of monomers with the same chirality.

In order to form the hydrogel of the present invention it is required that for a polymer chain, in order to contribute to the coherency of the gel structure, that it is grafted with at least two grafts. In this way a network can be formed.

The number of grafts is represented by the degree of substitution (DS) of the water soluble or water dispersible polymer. A DS of 100 refers to a polymer in which each monomeric unit of the polymer is substituted by a graft, whereas a DS of 0 refers to an ungrafted polymer. A minimum DS is required for a gel to be formed. DS can be varied by changing the synthesis conditions, in particular the conditions during the coupling of the grafts to the polymer. This can be carried out for example, by changing the ratio of oligomeric grafts/polymer in the synthesis mixture. Other parameters which may be used to control DS comprise reaction temperature and reaction time. As explained in the previous hereinabove, the minimum DS, for the portion of the polymer chains that contribute to the gel structure, should correspond to two grafts per polymeric chain.

On the other hand, in order for the constituent to be water soluble or water dispersible, it is required that DS is not too large. The value of DS required for the desired solubility or dispersability can be experimentally obtained in an experimental procedure which procedure per se is standard for the person skilled in the art. Preferably the number of grafts per polymer chain is larger than 2, more preferably it is between 2 and a number that corresponds to a DS of about 25. The corresponding value of DS will depend on the molecular weight of the polymer.

In a preferred embodiment of the hydrogel composition according to the present invention, the average degree of substitution of the water dispersible polymer with oligomeric or co-oligomeric groups is sufficiently high to obtain a network in which the crosslinks are formed by physical interaction of the water soluble or water dispersible polymers.

Preferably, the average degree of substitution is sufficiently low to render the polymeric structure water soluble or water dispersible.

The graft length is represented by the degree of polymerization (DP), which is the amount of monomers that constitute a graft. DP can be varied by changing the synthesis conditions, e.g. by changing the initiator/graft monomers ratio.

The DP should be sufficiently high in order for the grafts to interact so that a gel can be formed. On the other hand, when the grafts are too long, the water solubility or water dispersibility becomes insufficient. Typically, for a poly(lactic acid) graft the average DP is greater than 6, more preferably it is between 7 and 25, but of course this value will depend on the type of oligomer used as graft as well as on the type of polymer.

For a hydrogel that comprises or is comprised of water soluble polymers, such as dextran polymers, part of which are grafted with poly(D-lactic acid) and the other part with poly (L-lactic acid), the lower value of DS is preferably a value that corresponds to 2 grafts per polymer chain. The upper value is preferably about 25, and average DP is between 6 and 25. Preferably both said parts are equal.

It will be understood that the preferable values for DS and DP depend essentially on the type of grafts and the required properties of the resulting gel, although also the type of polymer used and other conditions can be of influence. For example, when the oligomeric or co-oligomeric groups of one mixture comprise poly(D-lactic acid) and the oligomeric or co-oligomeric groups of the other mixture of the hydrogel composition according to the invention comprises poly(L-lactic acid), it is preferred that both oligomeric or co-oligomeric groups have an average chain length of 7-25 monomers.

In fact, the release properties and other properties of the resulting gel, when applied in controlled release, can be fine-tuned and adopted to a specific application by varying DP and DS, which is a tremendous advantage of the present invention.

It is also possible that the grafts are co-oligomers of different monomers, as long as at least one of the monomers used has a chirality that is opposite from at least one of the monomers that is used in the grafts of the polymer of the other system.

In one embodiment of the present invention, the grafts of the polymer in system (A) are in essence formed from the L-enantiomers of a monomer and the grafts of the polymer in system (B) are in essence formed from D-enantiomers of the same monomer.

In a preferred embodiment of the hydrogel according to the present invention, the said oligomers or co-oligomers of mixtures (A) or (B) are chosen from the group comprising homo-oligomers of D-lactic acid, random co-oligomers of D-lactide/s-caprolactone, di- and triblock blends of D-rich poly (lactic acid), poly(D-lactide-co-glycolide), di- and triblock co-oligomers of poly(ethylene glycol)/poly(D-lactic acid), poly(methyl methacrylate), poly($\alpha$-methyl-$\alpha$-ethyl-$\beta$-propiolactone), poly(tert-butylethylene oxide), poly(tert-butylethylene sulfide), poly[$\beta$,-(1,1-dichloropropyl)-$\beta$-propiolactone], poly($\alpha$-benzyl glutamate), poly(methylbenzyl methacrylate), poly(vinyl-N-butylpyridium bromide), poly (sodium styrenesulfonate), poly(tert-butylthiirane), poly($\alpha$-methylbenzyl methacrylate), poly[$\beta$-(1,1-dichloroethyl)-$\beta$-propiolactone], and mixtures thereof; and said monomers of the other mixture are formed by the enantiomers of said monomers of the first mixture.

In another preferred embodiment the water soluble or water dispersible polymer of the hydrogel of the present invention is chosen from the group consisting of dextran, starch, cellulose derivates, albumin, lysozym, poly(aminoacids), poly(lysine) and related copolymers, poly(glutamic acid) and related copolymers, poly((meth)acrylates)/((meth) acrylamides), poly(vinylalchohol), poly(ethylene glycol), water soluble polyphosphazenes, or mixtures thereof.

When applied as a controlled release system, the drug to be released is incorporated after the formation of the gel, viz. after the addition of mixtures (A) and B.

Alternatively, because the gel of the present invention is prepared in the absence of organic solvents, the drug to be released can be added to the composition prior to the formation of the gel, viz. prior to the addition of system (A) and system (B). The drug is thus mixed with system (A) and/or system B, which systems are subsequently mixed, upon which the gel will be formed under suitable reaction conditions.

The graft groups can be linked directly to the polymers or by means of a linking group, depending on the reactivity of the groups and the polymer. An example of such a linking group is carbonyldiimidazole (CDI). Such linking groups are converted further when the grafts are linked to the polymer. The linking group could also be applied to enhance the biodegradability of the product. According to a preferred embodiment of the present invention there is a linking group between the water soluble or water dispersible polymer and the oligomeric or co-oligomeric group, which linking group comprises a hydrolysable group.

The grafts can be formed by oligomerization of the monomers, which is preferably carried out by using an initiator. The initiator is usually incorporated in the oligomeric graft. Such initiators are compounds with a primary or secondary hydroxyl group, e.g.: ethyl lactate or other aliphatic or aromatic lactate esters, benzyl alcohol, lauryl alcohol, 1,4-butanediol, adipic acid, (monomethoxy)PEG, 2-(2-methoxyethoxy)ethanol, or mixtures thereof. Care should be taken that the use of these initiators does not give rise to toxic levels of (reaction products of) these initiators in the resulting gel when applied in vivo. For this reason it is preferred to use endogenous compounds or compounds derived from endogenous compounds as an initiator. The use of such compounds as initiator prevents unacceptable (i.e. toxic) levels of these compounds or the reaction products thereof. An example of a suitable initiator is ethyl lactate, which is easily hydrolyzed to the relatively harmless compounds ethanol and lactate in e.g. mammals.

When an initiator is applied, the grafts in the resulting product may carry (part of) the initiator as an end group. The amount of initiator relative to the amount of graft monomers can be used to tailor the value of DP.

The oligomerization is carried out in the presence of a suitable catalyst. Such a catalyst can be chosen from the group comprising: stannous octoate, aluminum alkoxides (e.g., aluminum tris(2-propanolate), zinc powder, $CaH_2$, Sn(IV)tris-2-ethylhexanoate, tetraphenylporphinatoaluminum, aluminum triisopropoxide, chiral Schiff's base/aluminum alkoxides, Al(Acac), SALEN-Al—$OCH_3$, t-BuOLi, $Bu_3SnOCH_3$, PbO, zinc oxide, diethyl zinc, zinc chloride, stannous chloride, magnesium salt, Zn(Acac), $ZnEt_2$-Al $(OiPr)_3$, $(ZnEt_2+AlEt_3+nH_2O)$, yttrium oxide, or mixtures thereof.

The grafting of the polymers can be effected by mixing the grafts with or without the linking groups and the polymers in a suitable solvent. Preferably the grafts are mixed with the linking groups. Such solvents can be chosen from aprotic solvents, depending on the polymer used, e.g. dimethyl sulfoxide for e.g. polydextrans, after which the grafting reaction is carried out under suitable conditions, which conditions can be easily determined by a skilled person. After this the solvent is removed.

The degree of substitution can be controlled by changing the amount of (co-)oligomeric graft and water soluble polymer, e.g. the ratio of lactides to dextran.

Another parameter that can be used in the hydrogels according to the present invention is the presence of (co-) oligomers in the hydrogel which are not grafted to the polymer. Such non-bonded (co-)oligomers form physical interaction, which interaction is similar as described in the above. The non-bonded (co-)oligomers interact with the grafts present on the polymer, thus 'occupying' the grafts and consequently reduce the interaction between the different polymer chains through the grafts, rendering a gel which is softer and/or has a lower shear modulus.

The oligomeric groups can be coupled to the polymer by a coupling reaction, e.g. by forming a carbonate or ester bond between hydroxyl moieties present on the polymer with hydroxyl groups (carbonate bond) or carboxylic acid groups (ester bond) of the oligomeric groups.

Some oligomeric groups which find particular use in the present invention are bifunctional, i.e. have two functional groups with which the coupling to the polymer can be carried out. Lactic acid oligomers, for example, bear a hydroxyl group on one end and a carboxylic acid group on the other end of the chain. This carboxylic acid end group may be in its free form or may be blocked, e.g. in the form of an ester with a group derived e.g. from the initiator.

Stereocomplexes may be formed from a mixture of such oligomers (i.e. the non-bonded oligomeric groups per se), i.e. a racemic mixture of oligomers formed from D-monomers and oligomers formed from L-monomers (which will be referred to as "D-oligomers" and "L-oligomers", respectively). It is found that the stereocomplex formation takes place in either the so-called parallel or anti-parallel orientation of the chirally different oligomers.

In stereocomplexes with the parallel orientation each D-oligomer is paired with an L-oligomer, such that the beginning ($\alpha$-position) of each D-oligomer is next to the $\alpha$-position of an L-oligomer with which it forms the stereocomplex. Likewise, the end position ($\omega$-position) of the chirally different oligomers are paired $\omega$-$\omega$.

In anti-parallel stereocomplexes, however, the D-oligomers show a preference for pairing such that their $\alpha$-position is next to the $\omega$-position (end position) of the L-oligomers.

Whether parallel or anti-parallel stereocomplexes are formed, depends mainly on the type of oligomers, viz. the monomers used to make these oligomers. For example, in a mixture of poly(D-lactide) and poly(D-lactide), a poly(L-lactide) segment and poly(D-lactide) segment are packed in parallel fashion (Okihara, T.; Tsuji, M.; Kawaguchi, A.; Katayama, K. I.; Tsuji, H.; Hyon, S. H.; Ikada, Y. J. *Macromol. Sci. Phys.* 1991, B30(1&2), 119-140).

It was found that this preference for parallel or anti-parallel orientation of the oligomers can be employed to obtain a hydrogel which has particular favorable rheological behavior.

For example, a hydrogel can be prepared from a mixture (A) and (B) as described above of polymers grafted with groups derived from bifunctional oligomers that show preference to parallel orientation. When the majority of the oligomeric groups on the polymers in mixture (A) are linked to the polymer through a moiety (for example the moiety at the $\alpha$-position), while the oligomers in mixture (B) are linked to the polymer through the moiety at the opposite position of the bifunctional oligomer (i.c. the moiety at the $\omega$-position), a mixture is obtained which shows enhanced gel formation, viz. stronger gels (higher value of G') compared with polymers grafted with oligomeric groups which are linked to the polymer by the same functional group in both mixtures (A) and (B), having the same DP and DS.

By choosing the synthesis conditions for grafting the polymers in mixture (A) differently from the synthesis conditions for grafting the polymers in mixture (B), a gel can be obtained in which the parallel orientation of the oligomeric groups is facilitated. When the parallel orientation of the corresponding oligomers is preferred, this will result in a stronger gel than when the same oligomeric groups are in anti-parallel orientation (which orientation is facilitated by employing the same synthesis conditions for grafting in both mixtures).

Conversely, when grafts are used derived from oligomers that form anti-parallel stereocomplexes, the stronger gel is obtained when synthesis conditions for grafting are the same in both mixtures.

Therefore, according to a further embodiment of the invention, there is provided a hydrogel composition as described above, in which the oligomeric groups are derived from bifunctional oligomers that form parallel stereocomplexes, in which a substantial part of the oligomeric groups are coupled to the polymer in mixture (A) through a chemical moiety that is different from the corresponding moiety through which a substantial part of the oligomeric groups are coupled to the polymer in mixture (B).

Conversely, when anti-parallel oligomeric groups (i.e. groups derived from oligomers that form anti-parallel stereocomplexes) are employed, stronger gels are obtained when the groups are coupled to the polymer in mixtures (A) and (B) through the same group. Coupling through different groups, as described above, could in this case be employed to lower the strength (value of G') of the resulting gels.

Facilitating the parallel or anti-parallel orientation of the oligomeric groups can be obtained easily by choosing proper synthesis conditions. For example, when polymers having hydroxyl groups are used in mixtures (A) and (B) and parallel complexing oligomers are used as oligomeric groups, which oligomers are bifunctional in that they have an hydroxyl group on one end and a carboxylic acid group on the other end, the skilled person can choose synthesis conditions in mixture (A) which result in the formation of a carbonate bond. The carbonate bond is formed between the hydroxyl group of the oligomeric group and the hydroxyl group of the polymer. The synthesis conditions in mixture (B) can be chosen such that an ester bond is formed between the carboxylic acid group of the oligomeric group and the hydroxyl group of the polymer. When the two mixtures (A) and (B) are subsequently mixed together, gel formation is enhanced by the anti-parallel orientation of the oligomeric groups.

Prior to mixing (A) and (B) the individual mixtures can be subjected to solvatation, which comprises mixing for a certain period of time.

An interesting possible use of the invention is the use of mixture (A) and (B) for the in vivo formation of the hydrogel. When mixtures (A) and (B) are mixed, the resulting mixture will initially be liquid, since the formation of a hydrogel will take some time. When this mixture is injected before the formation of a hydrogel is completed, the hydrogel will be formed in vivo. This is carried out by mixing ex vivo the mixtures (A) and (B) and injecting this mixture in liquid form after which said hydrogel forms in vivo.

The stereocomplex hydrogels according to the present invention, are macroscopic gels. The gels can be used in their macroscopic form, applied e.g. in implants. The stereocomplex hydrogels may also be used for topical application in which an active ingredient can be administered, by applying the drug loaded gel to skin. This can be used e.g. in the treatment of burns and scalds.

Alternatively, the gels can be formed in microspheres, for example by spray drying. Another possibility for forming microspheres is described in PCT/NL97/00625 which discloses a two phase method in which a two phase system is formed from two incompatible water soluble polymers and at least one releasable compound. According to the present invention, a process for the preparation of a hydrogel in the form of microspheres comprises the formation of a two phase system, optionally in the presence of a releasable compound, by choosing two of said water soluble or water dispersible polymers such that they are incompatible; from which two phase system the hydrogel is formed.

Injectable microspheres, suitable for controlled release of an active ingredient, which is incorporated preferably before the gel formation takes place, can thus be obtained.

Another interesting application of the gels of the present invention is to encapsulate cell material, in particular living cells. This is of particular interest for tissue engineering. This encapsulation can be effected by mixing the cells and/or another active ingredients, such as growth factors, in one of the mixtures (A) or (B), after which the other mixture is added, by which the gel is formed. Instead of cells, other biological or non-biological compounds can be used as active ingredient. Examples are plasmid DNA, viral vectors, and colloidal carriers such as liposomes, iscoms, polyplexes (i.e. combinations of (cationic) polymers—such as organic polyphosphazenes or polyacrylates—and DNA), lipoplexes (i.e. combinations of (cationic) lipids and DNA), nanoparticles, (i.e. polymer based spheres in the nanometer size range), solid lipid particles in the colloidal size range, emulsions, such as intralipid-like systems, and combinations thereof. Also low molecular weight compounds may be encapsulated.

The present invention also provides a process for the preparation of a hydrogel comprises the steps of preparing two mixtures of a substituted water soluble or water dispersible polymer, the preparation of each mixture comprising:

1) polymerization, optionally in the presence of a suitable initiator, of a monomer, where the monomer of one mixture is the enantiomer of the monomer of the other mixture.

2) reaction of the product of the previous step with a suitable coupling compound, 3) reaction of the product of the previous step with said water soluble or water dispersible polymer, and 4) mixing two said mixtures.

Preferably, the suitable initiator in step 1) contains a primary or secondary hydroxyl group.

The invention further relates to the use of two opposite enantiomeric forms of a monomer in an oligomer or co-oligomer which oligomer or co-oligomer are attached to polymeric chains to physically link these polymeric chains.

Whether a specific mixture of grafted polymers will give rise to the formation of a gel can effectively be assessed by measuring the rheologic behavior of the presence of physical interactions (stereocomplexes) will give rise to (more) elastic behavior, as is reflected for example in the storage modulus (G'), the loss modulus (G''), tan δ (=G''/G') and/or the creep, which can be determined experimentally.

The present invention will now be illustrated in the following Examples, which are not intended to limit the scope of the invention.

EXAMPLE 1

Synthesis of Dex-Lactate ($(DP)_{av}$=15, $(DS)_{av}$=10) Hydrogels

Ringopening polymerization of lactide (L-lactide for system (A) and D-lactide for system B, each 5 g) was carried out using 2-(2-methoxyethoxy)ethanol (MEE, 0.556 g) as an initiator, and stannous octoate (0.093 g) as the catalyst. The polymerization was carried out in the melt at 130° C. for four hours to yield MEE-L-lactic acid oligomer (A) and MEE-D-lactic acid oligomer (B). FIG. 1 shows the reaction scheme for the synthesis of dex-lactate (8), in which the DP is the degree of polymerization and DS is the degree of substitution (number of lactic acid oligomers per 100 glucopyranose units of dextran.

Subsequently, carbonyldiimidazole (CDI, 1.122 g, 2 eq., 6.92 mmol) was dissolved in tetrahydrofuran (THF) in a nitrogen atmosphere. The MEE-lactates (A) and (B) (each 4 g, 3.46 mmol) from the previous step were added in THF to form separate CDI mixtures. Each reaction mixture was stirred for four hours at room temperature under nitrogen atmosphere. The products were purified by precipitation in water to inactivate residual CDI. After centrifugation the product was dissolved in acetonitrile and dried over $MgSO_4$. After filtration, the organic solvent was removed under reduced pressure, yielding a viscous oil for each mixture (A) and (B). Both products (A) and (B) were dissolved in dried DMSO.

After this, two mixtures were made in which dextran (5.6 g) was dissolved in dry dimethyl sulfoxide (DMSO) before 4-(N,N-dimethylamino)pyridine (DMAP, 1.06 g, 0.25 eq. to dextran, 8.65 mmol) was added. After dissolution of DMAP, the MEE-lactate-carbonylimidazole mixtures (A) and (B) (each 4.48 g, 3.46 mmol) of the previous step were each added to one portion to yield two new mixtures (A) and (B). These mixtures were stirred at room temperature for 4 days under nitrogen atmosphere, after which the reaction was stopped by adding concentrated HCl to neutralize DMAP and imidazole. The reaction mixtures were dialyzed against demineralized water at 4° C. The crude dex-lactate products were lyophilized and the uncoupled lactate oligomers were removed by extraction with dichloromethane. After filtration and evaporation the pure product was obtained.

The products had grafts with an average degree of polymerization $(DP)_{av}$ of 15 and the average degree of substitution of the polymer $(DS)_{av}$ was 10.

80% hydrogels were prepared by blending a mixture of 200 mg of product (A) from the previous step in 800 μl acetate buffer, pH=about 4 (in order to minimize hydrolysis), with product (B) (also 200 mg/800 μl acetate buffer, pH=about 4) in equal amounts. Before blending the individual products were dispersed during three days at room temperature.

EXAMPLE 2

Synthesis of Dex-Lactate ($(DP)_{av}$=9, $(DS)_{av}$=10) Hydrogels

The procedure of Example 1 was repeated, but different amounts of reactants were used instead: L(or D)-lactide (10 g), MEE (1.85 g, 0.015 mol), stannous octoate (0.3 g, 0.74 mmol, 5 mol % to MEE).

From the product of this first step 4.23 g (5.5 mmol) was used with CDI (1.79 g, 2 eq., 11 mmol).

The dex-lactate-MEE was obtained using the product of the previous step (5.32 g, 6.17 mmol) and DMAP (1.88 g, 0.25 eq., 15 mmol).

The products had grafts with an average degree of polymerization $(DP)_{av}$ of 9 and the average degree of substitution of the polymer $(DS)_{av}$ was 10.

The remainder of the procedure was similar to that of Example 1.

EXAMPLE 3

Rheology Behaviour

The rheology of samples prepared in the previous Examples was studied. The mixtures (A) and (B) from the previous Examples were either solvatated before they were mixed, in which they were stirred for a certain period of time, or mixed directly.

Upon mixing (A) and B, the gel formation was followed with a rheometer (TA Instruments AR 1000-N) using a 2 cm, 1 degree steel cone plate and a solvent trap filled with silicon oil of 100 mPa·s, at a frequency of 1 Hz. The measurements were performed in controlled strain mode, in which the force to obtain a deformation of 1% is measured. The results are expressed as the storage modulus G', which represents the elastic storage of energy in the sample. For a real Newtonian fluid, G' will be zero. A higher value of G' corresponds to a gelled structure. By definition, tan δ=1 defines the sol-gel transition. A value of tan δ smaller than 1 also indicates gel formation. Generally, the gels which are obtained in accordance with the present invention have a value of tan δ which is smaller than 0.3.

Typical rheograms for a 20 wt % dextran-L-lactate (average DP=15 (FIG. 2) or 9 (FIG. 3)) in water as well as a mixture of 10 wt % dextran-L-lactate (average DP=15 (FIG. 2) or 9 (FIG. 3)) and 10 wt % dextran-D-lactate (average DP=15 (FIG. 2) or 9 (FIG. 3)) in water are shown.

The mixture of the L and D forms (mixture (A) and B) showed an increase of G' as a function of time, whereas one enantiomeric form of dex-lactate product did not show such an increase. The increase of G' in case of the mixture of (A) and (B) shows that the product becomes more and more elastic. This phenomenon was not observed with one enantiomeric form. This is explained by the formation of stereocomplexes between two enantiomeric forms.

TABLE 1

Storage moduli of dex-lactate products of Example 1 and 2.

| $(DP)_{av}$[1] | $(DS)_{av}$[2] | Enantiomeric form | G' (Pa) after 2-3 minutes | G' (Pa) after 15 h |
|---|---|---|---|---|
| 9 | 5 | L and D (blend) | 1323 | 3680 |
| 9 | 5 | L and D (blend) | 2059 | 3184 |
| 9 | 5 | L or D[3] | 629 | 683 |
| 15 | 4 | L and D (blend) | 4049 | 8384 |
| 15 | 4 | L and D (blend) | 3453 | 7934 |
| 15 | 4 | L or D[3] | 1972 | 2306 |

[1] average degree of polymerization
[2] average degree of substitution
[3] reference

TABLE 2

Development of storage moduli in time of dex-lactate products of Example 1 with $(DP)_{av}$ = 15.

| Solvatation time (h) | a[1] G'[2] (Pa) | a[1] G'[3] (Pa) | b[1] G'[2] (Pa) | b[1] G'[3] (Pa) | c[1] G'[2] (Pa) | c[1] G'[3] (Pa) | d[1] G'[2] (Pa) | d[1] G'[3] (Pa) |
|---|---|---|---|---|---|---|---|---|
| 0 | | | | | | | 1972 | 2306 |
| 16 | 2402 | | | | 1823 | 6039 | | |
| 40 | | | | | 3453 | 7934 | | |
| 48 | 2359 | 4911 | 232 | 302 | | | | |
| 60 | 982 | 2383 | | | | | | |
| 62 | 1259 | 4064 | | | | | | |
| 68 | | | 1253 | 1476 | | | | |
| 72 | | | | | 1721 | 4432 | | |
| 80 | 1164 | 6717 | | | | | | |
| 95 | | | 1705 | 1715 | | | | |
| 96 | | | | | 3140 | 6084 | | |
| 100 | 1553 | 5026 | | | | | | |
| 120 | | | | | 2947 | 6639 | | |
| 144 | | | | | | | 1515 | 1903 |
| 240 | | | | | 2926 | 8459 | | |
| 264 | | | | | | | 1323 | 1783 |

[1] a: Non-purified dex-lactate product containing non coupled oligomer, 1:1 Dex- (L) lactate and Dex- (D) lactate mixture (10 + 10 wt % gel). b: Reference; Non-purified dex-lactate product containing non coupled oligomer, Dex-(L) lactate or Dex-(D) lactate (20 wt % gel). c: Purified dex-lactate product, 1:1 Dex-(L) lactate and Dex-(D) lactate mixture(10 + 10 wt % gel). d: Reference; Purified dex-lactate product, Dex-(L) lactate or Dex-(D) lactate (20 wt % gel).
[2] Storage moduli measured 2-3 minutes after mixing.
[3] Storage moduli measured after gelation, viz. after 24-72 h.

TABLE 3

Development of storage moduli in time of dex-lactate products of Example 2 with $(DP)_{av}$ = 9.

| Solvatation time (h) | a[1] G'[2] (Pa) | a[1] G'[3] (Pa) | b[1] G'[2] (Pa) | b[1] G'[3] (Pa) | c[1] G'[2] (Pa) | c[1] G'[3] (Pa) | d[1] G'[2] (Pa) | d[1] G'[3] (Pa) |
|---|---|---|---|---|---|---|---|---|
| 0 | | | 550 | 727 | | | | |
| 48 | | | | | 1323 | 3680 | | |
| 60 | | | | | 2059 | 5067 | 529 | 683 |
| 156 | 275 | 1353 | | | | | | |
| 180 | 242 | 1276 | | | | | | |

TABLE 3-continued

Development of storage moduli in time of dex-lactate products of Example 2 with $(DP)_{av} = 9$.

| Solvatation time (h) | a[1] | | b[1] | | c[1] | | d[1] | |
|---|---|---|---|---|---|---|---|---|
| | $G^{(2)}$ (Pa) | $G^{(3)}$ (Pa) | $G^{(2)}$ (Pa) | $G^{(3)}$ (Pa) | $G^{(2)}$ (Pa) | $G^{(3)}$ (Pa) | $G^{(2)}$ (Pa) | $G^{(3)}$ (Pa) |
| 252 | 176 | 1354 | | | | | | |
| 276 | 130 | 1917 | | | | | | |

[1]a: Non-purified dex-lactate product containing non coupled oligomer, 1:1 Dex-(L) lactate and Dex-(D) lactate mixture (10 + 10 wt % gel). b: Reference; Non-purified dex-lactate product containing non coupled oligomer, Dex- (L) lactate or Dex-(D) lactate (20 wt % gel). c: Purified dex-lactate product, 1:1 Dex- (L) lactate and Dex- (D) lactate mixture (10 + 10 wt % gel). d: Reference; Purified dex-lactate product, Dex-(L) lactate or Dex-(D) lactate (20 wt % gel).
[2]Storage moduli measured 2-3 minutes after mixing.
[3]Storage moduli measuxed after gelation, viz. after 24-72 h.

Figure 2:
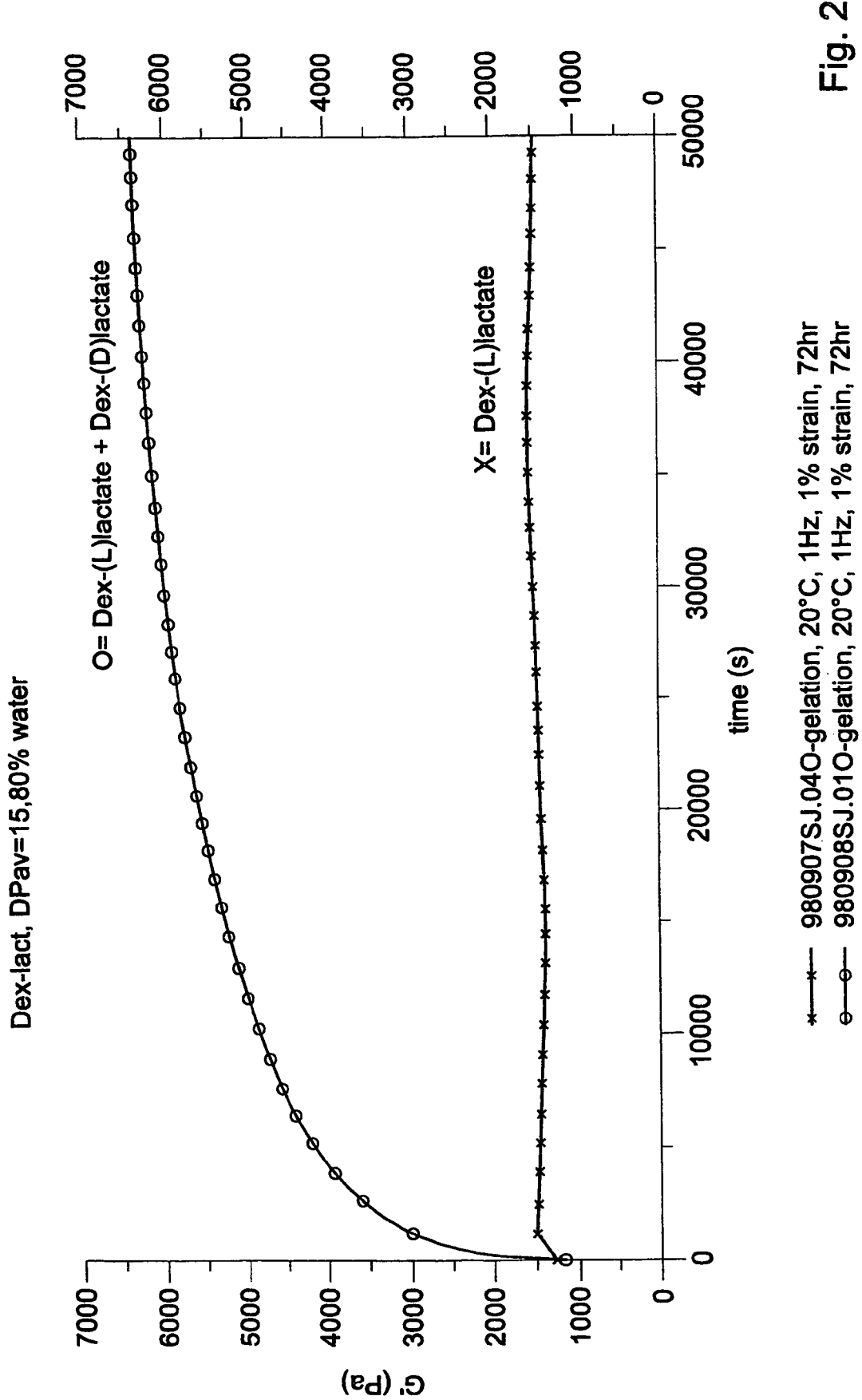
Figure 3:
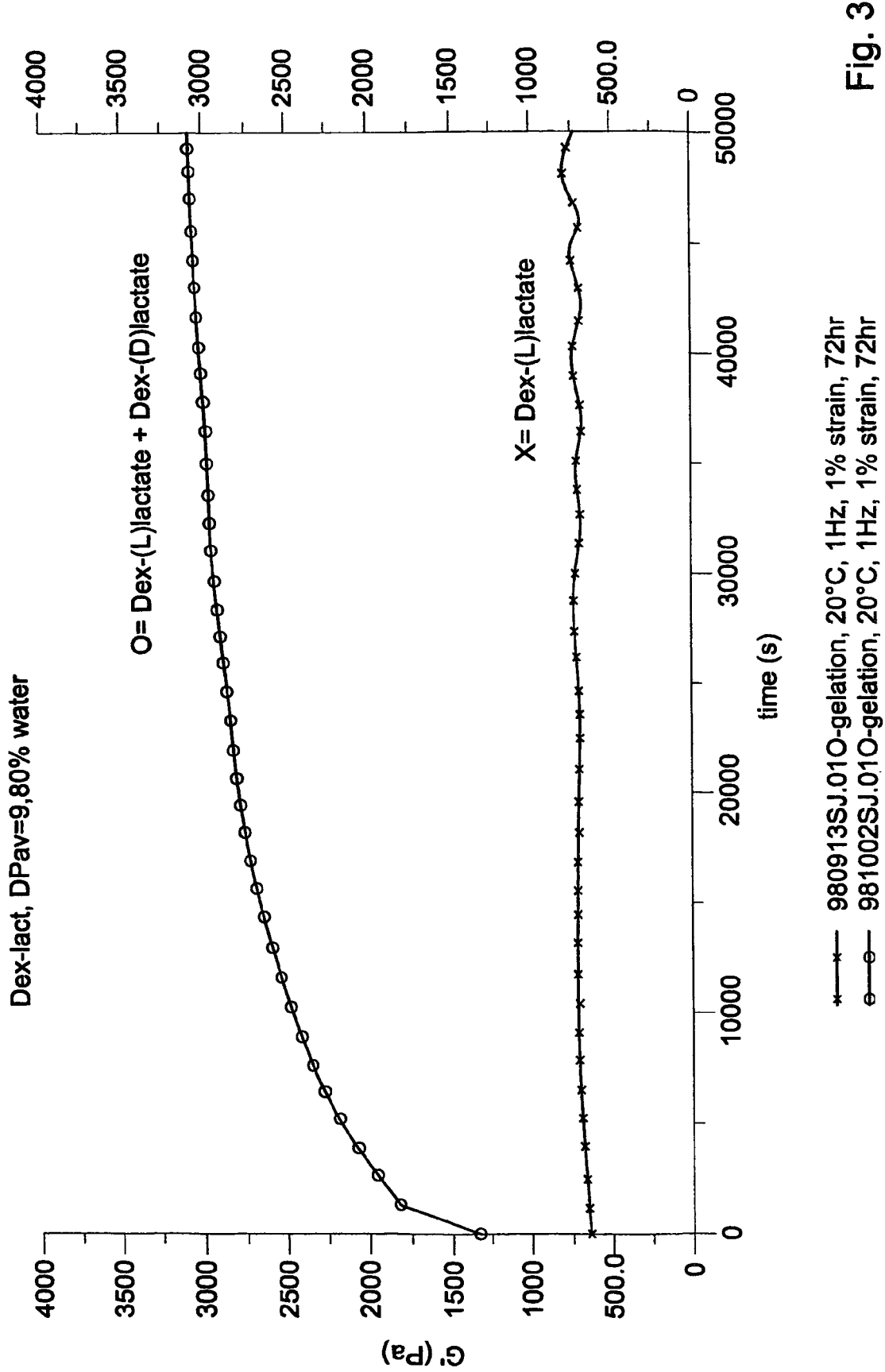

The experimental data in Tables 1-3 and FIGS. 2 and 3 clearly demonstrate the different rheology behaviour of the hydrogels of the present invention when compared with the reference examples ('L or D' in Table 1 and experiments 'b' and 'd' in Table 2 and 3).

Moreover, the purified examples according to the present invention ('c' in Table 2 and 3) show higher storage moduli when compared with the unpurified samples according to the present invention ('a' in Table 2 and 3).

Finally, a longer solvatation time gives rise to formation of a gel with a higher final value of the modulus.

EXAMPLE 4

Synthesis, Characterization and Properties of Dex-(L) Lactate/Dex-(D)Lactate Gels Materials. L-Lactide ((3S-cis)-3,6-dimethyl-1,4-dioxane-2,5-dione, >99.5%) and D-lactide ((3R-cis)-3,6-dimethyl-1,4-dioxane-2,5-dione, >99.5%) were obtained from Purac Biochem BV (Gorinchem, The Netherlands) and used without further treatment. Stannous octoate (tin(II) bis(2-ethylhexanoate), $SnOct_2$, 95%) (Sigma Chemical Co., St. Louis, Mo., USA), dichloromethane, potassium peroxydisulfate (KPS) (Merck, Darmstadt, Germany), and 2(2-methoxyethoxy)ethanol (Aldrich-Chemie, Steinheim, Germany) were used as received. Tetrahydrofuran (THF) and acetonitrile (HPLC-S, gradient grade) were purchased from Biosolve LTD (Valkenswaard, The Netherlands). THF was distilled from $LiAlH_4$ immediately before use. Dextran (from *Leuconostoc mesenteroides*, $M_n$=15,000 Da, and $M_w$=32,500 Da, as determined by GPC analysis), dimethyl sulfoxide (DMSO, <0.01% water), glycidyl methacrylate (GMA, (±)-2,3-epoxypropyl methylpropenoate, 95% by GPC), N,N,N',N'-tetramethylethylenediamine (TEMED) and silicon oil (DC 200, 110 mPa·s), were obtained from Fluka Chemie AG (Buchs, Switzerland). 4-(N,N-dimethylamino)pyridine (DMAP, 99%) and N,N'-carbonyldiimidazole (CDI, 98%) were from Acros Chimica (Geel, Belgium). Dialysis tubes (cellulose, molecular weight cut off 12,000-14,000 (based on proteins)) were purchased from Medicell International Ltd. (London, UK). Methacrylated dextran (dex-MA) with a degree of substitution (DS, the number of methacryl residues per 100 glucopyranose units of dextran) of 4 was synthesized according to the procedure described in detail in Van Dijk-Wolthuis, W. N. E.; Franssen, O.; Talsma, H.; Van Steenbergen, M. J.; Kettenes-van den Bosch, J. J.; Hennink, W. E. Macromolecules 1995, 28, 6317-6322. Van Dijk-Wolthuis, W. N. E.; Kettenes-van den Bosch, J. J.; Van der Kerk-van Hoof, A.; Hennink, W. E. Macromolecules 1997, 30, 3411-3413.

Synthesis of polydisperse lactic acid oligomers. Lactic acid oligomers with varying DP were synthesized by a ring opening polymerization reaction of lactide with 2(2-methoxyethoxy)ethanol (MEE) and stannous octoate as initiator and catalyst, respectively, according to De Jong et al. (De Jong, S. J.; Van Dijk-Wolthuis, W. N. E.; Kettenes-van den Bosch, J. J.; Schuyl, P. J. W.; Hennink, W. E. Macromolecules 1998, 31, 6397-6402). The average degree of polymerization $(DP_{av})$ of the formed MEE-lactate was controlled by the MEE/lactide ratio.

Preparation of Monodisperse Lactic Acid Oligomers. Monodisperse lactic acid oligomers were prepared by fractionation of polydisperse MEE-lactate with preparative HPLC (column: Econosphere C8, 10 micron, 250×22 mm; Alltech, Illinois, USA) with an AKTA purifier (Pharmacia Biotech AB, Sweden). Polydispers oligomer (1 g) was dissolved in 1 ml water/acetonitrile (50 w/w %) and 500 µl of this solution was injected onto the column. A gradient was run from 100% A (water/actonitrile 95:5) to 100% B (acetonitrile/water 95:5) in 50 minutes. The flow rate was 5.0 ml/min; detection by UV (λ=195 nm). The chromatograms were analyzed with Unicorn Analysis module (version 2.30) software. The individual oligomers were collected and fractions with corresponding DP were pooled. The solvent was removed under reduced pressure. The oligomers were characterized by HPLC, NMR and MS.

Synthesis of activated lactic acid oligomer. To couple the oligomers to dextran, the hydroxyl group of the oligomer was activated using N,N'-carbonyldiimidazole (CDI). Essentially the same procedure was used as for the synthesis of hydroxyethyl methacrylate (HEMA)-lactate-CI. In brief, CDI (3.6 g, 22 mmol, 2 eq.) was dissolved in dried tertrahydrofuran (THF, 100 ml) in a nitrogen atmosphere. MEE-lactate (e.g. $DP_{av}$ 9; 8.46 g, 11 mmol, 1 eq.) was dissolved in THF (10 ml) and added to the CDI solution. The reaction mixture was stirred for four hours at room temperature in a nitrogen atmosphere. Thereafter, dichloromethane (DCM, 200 ml) was added and the reaction mixture was washed with water (100 ml), to decompose the excess of CDI and to remove the imidazole. Next, the water layer was extracted with DCM (50 ml) for two times. The organic layers were combined and dried over magnesium sulfate. After filtration, the organic solvent was removed under reduced pressure to yield the MEE-lactate-CI $DP_{av}$ 9.

$^1$H NMR ($CDCl_3$): δ 8.16 (m, 1H, C(O)—N—C$\underline{H}$=N), 7.44 (m, 1H, C(O)—N—C$\underline{H}$=CH), 7.07 (m, 1H, C(O)—N—CH=C$\underline{H}$), 5.35 (q, 1H, C$\underline{H}$—O—C(O)—N), 5.23-5.12 (overlapping q, C$\underline{H}$), 4.28 (m, 2H, C$\underline{H}_2$—O—C(O)), 3.66 (m, 2H, $CH_3$—O—C$\underline{H}_2$), 3.60 (m, 2H, C$\underline{H}_2$—O), 3.51 (m, 2H, C$\underline{H}_2$—O), 3.37 (s, 3H, C$\underline{H}_3$—O), 1.72 (d, C$\underline{H}_3$—CH—O—C(O)N), 1.63-1.50 (overlapping d, CH—C$\underline{H}_3$)

$^{13}$C NMR ($CDCl_3$): δ 169.5 $\underline{C}$=O, 168.8 $\underline{C}$(O)—N, 137.1 N—$\underline{C}$H—N, 121.6+117.1 N—$\underline{C}$=$\underline{C}$—N, 71.7 $\underline{C}H_2$, 71.5 ($CH_3$) $\underline{C}H$—O—C(O)—N, 70.3 $\underline{C}H_2$, 69.3-68.7 $\underline{C}H$—$CH_3$+$\underline{C}H_2$—$OCH_3$, 64.3 $\underline{C}H_2$—O—C(O), 58.9 $\underline{C}H_3$O, 25.5 $\underline{C}H_3$—CH—O—C(O)—N, 16.6/16.5 $\underline{C}H_3$ Synthesis of Dex-lactate. Dextran-lactate (dex-lactate) was synthesized using the same procedure as for the synthesis of dex-lactate-HEMA. In brief, dextran 40 000 (10 g) and DMAP (2 g, 16.3 mmol, 0.25 eq. to glycopyranose units of dextran) were dissolved in dried DMSO (90 ml). Next, MEE-lactate-CI (e.g. $DP_{av}$ 9, 5.7 g, 6.17 mmol) dissolved in dry DMSO (5 ml) was added. The solution was stirred at room temperature for 4 days in a nitrogen atmosphere, after which the reaction was stopped by addition of concentrated HCl (2 ml, 1 eq.) to neutralize DMAP and imidazol. The reaction mixture was extensively dialyzed against water (reversed osmosis) at 4° C. The dex-lactate product was collected by lyophilization. To remove traces of uncoupled lactic acid oligomers, the dex-lactate product (10 g) was extracted with dichloromethane (400 ml). The product was dried in a vacuum oven at 40° C., to yield dex-lactate with $DP_{av}$ 9 and degree of substitution (DS, the number of oligomers per 100 glucopyranose units of dextran) of 3. The DS was calculated by $^1$H NMR as $(x \cdot 100)/y$, in which x is the integral of the $CH_3$ groups of the lactic acid oligomer at 1.41 ppm divided by (3·DP), with DP is the degree of polymerization, and y is the integral of the anomeric proton of dextran at 5.14-4.95 ppm.

$^1$H NMR (12.5% $^2H_2O$/DMSO-$d_6$): δ 5.14-4.95 (broad m, residual OH, CH, CH—O—C(O)—N), 4.65 (broad s, anomeric proton dextran), 4.16 (m, 2H, CH$_2$—O—C(O)), 3.84-3.18 (m, (6H) dextran, (2H)CH$_3$—O—CH$_2$, (4H) CH$_2$—O, (3H) CH$_3$—O), 1.41 (overlapping d, C H$_3$—CH—O—C(O)N, CH—CH$_3$)

$^{13}$C NMR (12.5% $^2H_2O$/DMSO-$d_6$): δ 170.4 C(O)—O—CH$_2$, 169.8 C=O, 98.5 C$_{anomeric}$, 73.7 C$_3$, 72.1 C$_2$, 71.6 CH$_2$, 70.7 C$_5$, 70.3 C$_4$, 69.9 CH$_2$, 69.8 (CH$_3$) CH—O—C(O)—O-dex, 69.3 CH, 68.5 CH$_2$, 66.2 CH$_2$(dex), 64.8 CH$_2$, 58.5 CH, 20.6 CH$_3$—CH—O—C(O)—O-dex, 16.9 CH$_3$ Rheological experiments. For the rheological experiments two types of polymer solutions were prepared: one contains dex-(L)lactate and the other dex-(D)lactate. The dissolution time was at least one day at room temperature. Acetate buffer pH 4 was selected as solvent to prevent hydrolysis of the dex-lactate.

Equal amounts of the dex-(L)lactate and the dex-(D)lactate solutions were mixed, homogenized and quickly applied on the rheometer (AR 100 instrument of TA Instruments, Gent, Belgium). For most of the experiments a flat-plate measuring geometry (acrylic, 4 cm diameter; gap 1 mm) was used. A cone-plate measuring geometry (steel, 2 cm diameter with an angle of 1 degree; gap 31 μm) was used when only a small amount of material was available. Gelation of the dex-lactate solutions took place between the cone and plate of the measuring geometry. A solvent trap was used to prevent evaporation of the solvent. In addition, a thin layer of silicon oil (110 mPa·s) was applied to surround the dex-lactate sample thereby preventing evaporation.

Gelation of the mixture of dex-lactate solutions was monitored by measuring the shear storage modulus (G'), as well as the loss modulus (G") at 20° C. for 6 to 18 hours. A frequency of 1 Hz and a controlled strain of 1% were applied. The strain used in these experiments was as low as possible to minimize the influence of deformation on the formation of the dex-lactate hydrogels. At the end of gelation, two types of rheological measurements were done. Firstly, creep experiments were carried out to establish the visco-elastic properties of the samples. Therefore, a constant force (equal to the force applied at the end of the gelation measurement to obtain 1% deformation, which is in the linear visco-elastic range) was applied during 60 seconds while the strain was monitored. Secondly, the temperature was raised from 20° C. to 80° C. in 30 minutes while several rheological parameters were monitored (frequency 1 Hz, 1% strain). At 80° C., a creep experiment was carried out again. A constant force, equal to the force applied at 80° C. to obtain 1% deformation, was applied. Thereafter, the sample was cooled to 20° C. in 30 minutes while G' and G" were monitored (frequency 1 Hz, 1% strain), again followed by a creep experiment.

As a control, the same rheological experiments were performed with a solution of dex-(L)lactate. To compare the rheological behavior of physically cross-linked dex-lactate hydrogels with chemically cross-linked gels, measurements were performed on a hydrogel based on methacrylated-dextran (dex-MA). Dex-MA hydrogels were prepared by radical reaction of aqueous dex-MA solution (DS 4, 10 w/w % dex-MA in 0.01M phosphate buffer pH 7). Solution A was obtained by adding 50 μl TEMED (500 μl/ml, pH adjusted to 7) to 450 μl of a dex-MA solution, while solution B was a mixture of 410 μl dex-MA solution and 90 μl KPS solution (50 mg/ml in 0.01M phosphate buffer pH 7). 100 μl of solutions A and B were mixed and directly applied on the measuring geometry of the rheometer.

Rheology experiments were carried out in the same way as for the dex-lactate products.

NMR Spectrometry. NMR spectra were recorded with a Gemini 300 MHz spectrometer (Varian Associates Inc. NMR Instruments, Palo Alto, Calif., USA). Approximately 30 mg of lactic acid oligomer was dissolved in 0.8 ml deuterochloroform and 30 mg of dex-lactate was dissolved in a mixture of 0.8 ml dimethylsulfoxide-$d_6$ and 0.1 ml $^2H_2O$ (all solvents were obtained from Cambridge Isotope Laboratories, Andover, USA). For $^1$H NMR, chloroform (at 7.26 ppm) was used as the reference line, whereas for DMSO-$d_6$ the central DMSO line was set at 2.50 ppm. A pulse length of 4.5 μs (PW$_{90}$≈12 μs) was used with a relaxation delay of 15 s. For $^{13}$C NMR spectra, the pulse length was set at 4.5 ms (PW$_{90}$≈12 μs), and the relaxation delay at 2 s. The central line in the chloroform triplet at 76.9 ppm was used as the reference line, whereas for DMSO-$d_6$ (99.9% $^2$H, Cambridge Isotope Laboratories, Andover, USA) the central DMSO line was set at 39.5 ppm.

FTIR-transmission and Photoacoustic Spectroscopy (PAS). IR-transmission spectra of the lactic acid oligomers were recorded with a Biorad FTS-25 interferometer/spectrometer. Thin films of L-lactic acid oligomer, as well as the blend of L and D form, were casted from dichloromethane solutions onto a KBr tablet. The interferograms were recorded at a spectral resolution of 2 cm$^{-1}$ in the rapid-scan mode (5 kHz) with a deuterated triglycine sulfate (DTGS) detector. 32 scans were averaged to gain a good signal-to-noise ratio. Fourier transformation yields the IR-transmission spectra, which were normalized on background spectra obtained from the pure KBr tablet at an identical parameter set-up. IR-Photoacoustic (PA) spectra of dex-lactate were obtained with a Biorad FTS-6000 step-scan interferometer/spectrometer. After the rheology experiment, selected dex-lactate products were dried overnight at room temperature. The IR spectra of these products were measured with the PA detection method. The general benefit of this method is that no further preparation of the sample (i.e. the dex-lactate products) is needed. Therefore, IR spectra of solid materials can be obtained directly and rather quickly. The interferograms were recorded at a spectral resolution of 8 cm$^{-1}$ using a MTEC-200 photoacoustic detector. They were obtained in the step-scan mode of the interferometer, at 800 Hz stepping frequency of the moving mirror. Scanning in the step-scan mode of the interferometer resulted in a far better signal to noise ratio. 32 Scans were averaged, and Fourier transformed to yield the IR-PA-spectra of dex-lactate. All IR-PA spectra were normalized using the PA-reference-sample carbon black.

Results

Synthesis of the lactate grafted dextrans. In the synthesis of dex-lactate (FIG. 1) essentially the same strategy was used as for the synthesis of dex-lactate-HEMA. First, the lactide acid oligomer (3) was synthesized via a ring opening polymerization of lactide. After activation of the hydroxyl end-group with N,N'-carbonyldiimidazole (CDI, 4), the resulting lactate-CI (5) was coupled to dextran (7) to yield dex-lactate (8). The incorporation of the lactic acid oligomers under the standard reaction circumstances, 4 days reaction time at room temperature, was about 30%. Higher degrees of incorporation, up to 60%, could be achieved by longer reaction times (18-24 days) or higher reaction temperatures (80° C.). HPLC analysis demonstrated that under the selected reaction conditions no transesterification occurred.

Figure 4:
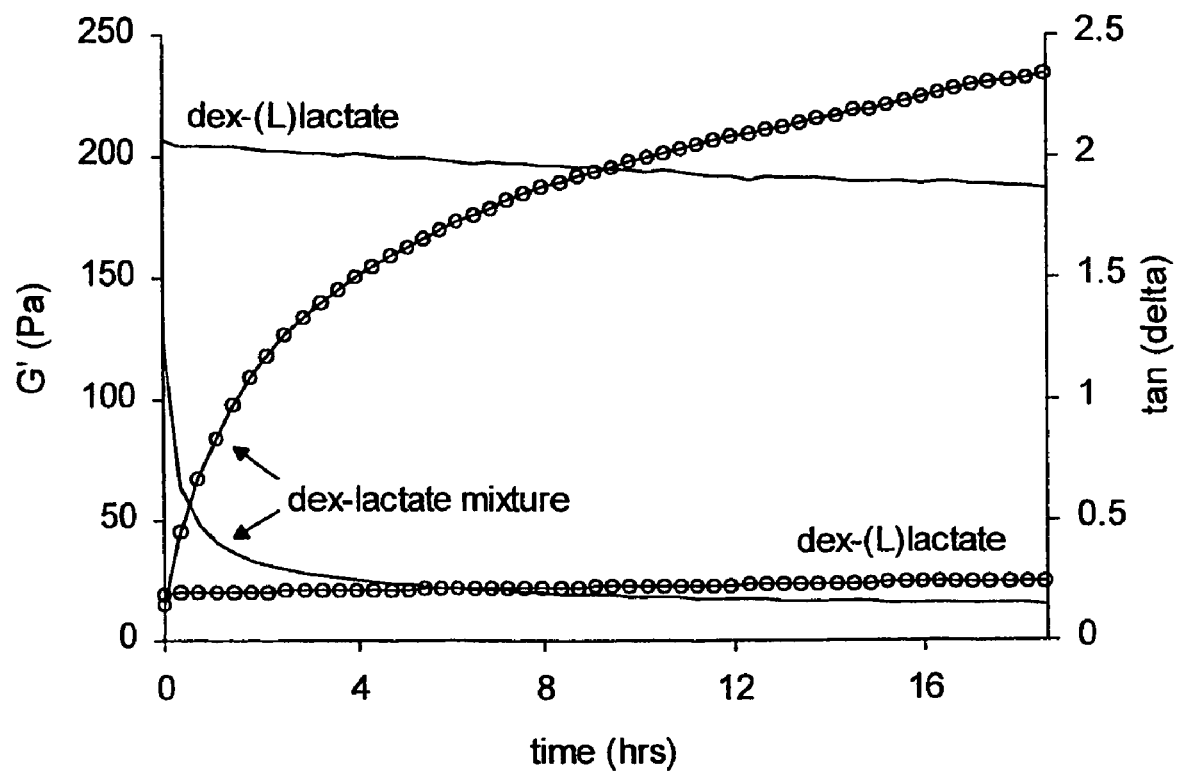

Gelation of dex-lactate solutions. FIG. 4 shows the rheological characteristics as a function of time of dex-(L)lactate solution and a mixture of dex-(L)lactate and dex-(D)lactate solutions. G' and tan δ of dex-(L)lactate did not change in time. In contrast, the dex-(L)lactate and dex-(D)lactate mixture showed an increase in G' (even after 18 hours no real plateau value was reached) and a dramatic decrease of tan δ (from 1.2 to 0.1) in time. The network formation can be attributed to association of the enantiomeric lactic acid chains (stereocomplex formation). The fact that no real plateau value of G' was reached is often observed in physically cross-linked networks, such as gelatin, see for example Bot, A.; Van Amerongen, I. A.; Groot, R. D.; Hoekstra, N. L.; Agterof, W. G. M. *Polymer Gels and Networks* 1996, 4, 189-227.

Figure 5A:
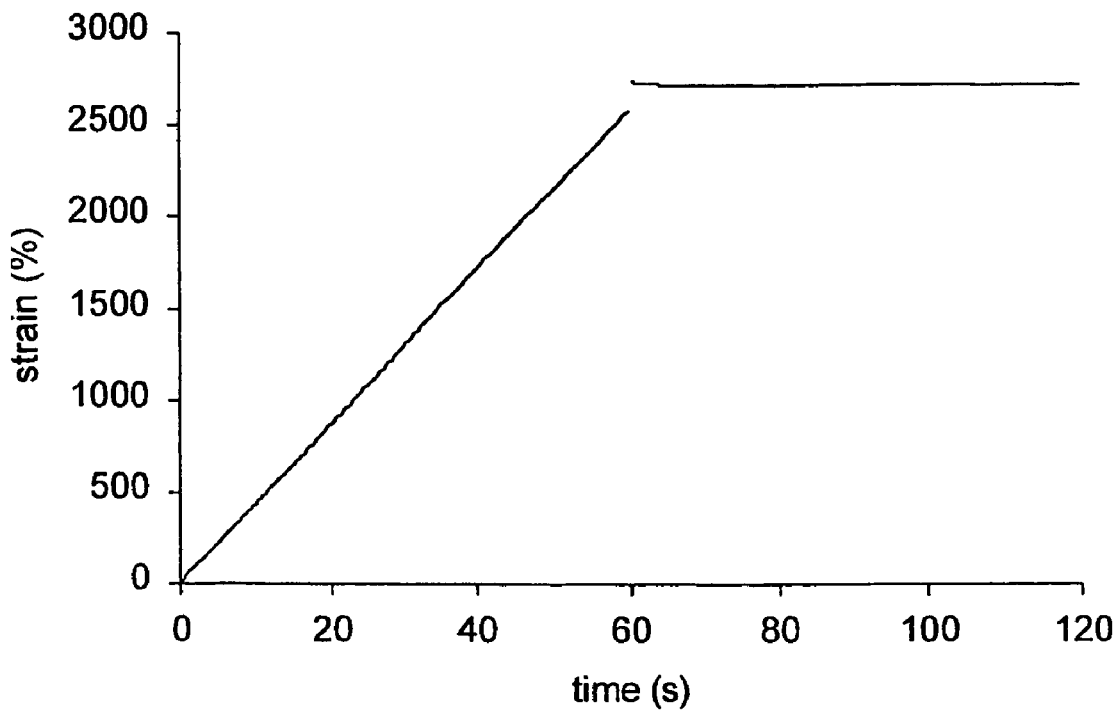
Figure 5B:
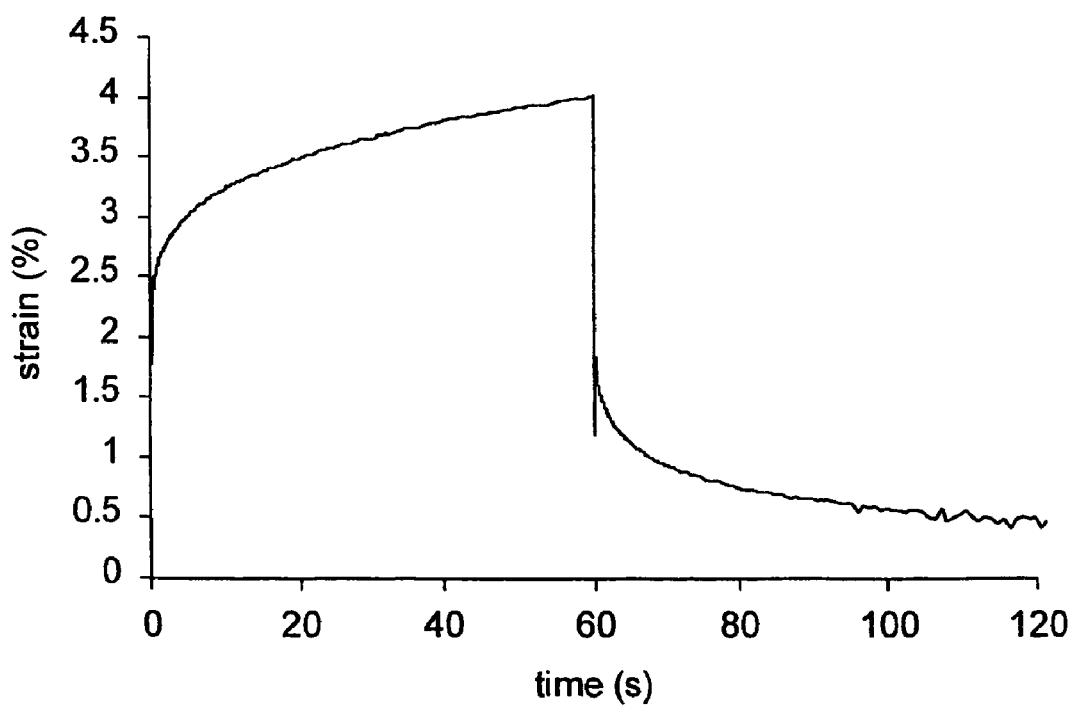

FIG. 5 shows the results of creep experiments on the samples of FIG. 4 after about 18 hours. The retardation profile shows full viscous behavior for dex-(L)lactate (FIG. 5A), which is in agreement with the high value of tan δ observed (FIG. 4). For the dex-lactate mixture elastic behavior was observed in the creep experiment (FIG. 5B), in agreement with the low value of tan δ (FIG. 4).

Figure 6:
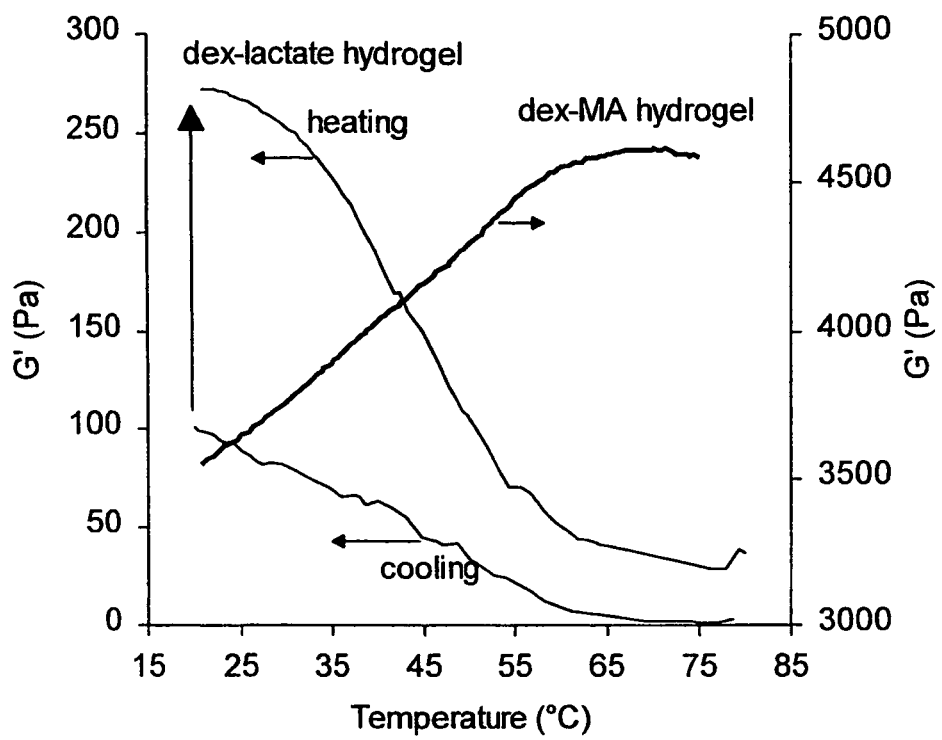

Thermoreversibility. The rheological characteristics of a chemically cross-linked methacrylated-dextran gel were monitored as a function of temperature. FIG. 6 shows that G' increased proportionally with temperature, which is in agreement with the rubber elasticity theory of Flory. At 80° C. the dex-MA hydrogel remained fully elastic as observed from a creep experiment (result not shown). During cooling the reverse G' profile was observed, and G' at 20° C. equaled G' before heating.

In contrast, the dex-lactate gels showed a completely different temperature dependency. Upon heating the dex-lactate hydrogels G' dropped (FIG. 6). The loss modulus (G") of the mixture at 80° C. was almost equal to the G" of a single isomer of dex-lactate (not shown), indicating that no cross-links were left in the mixture. Creep experiments of both systems at this temperature showed viscous behavior as in FIG. 5A. FIG. 6 shows that upon cooling G' increased and finally reached the original value of G' at 20° C., indicated by the vertical arrow. A creep experiment showed the same pattern as FIG. 5B, which proves the full thermo-reversible properties of the mixture of both isomers and the physical nature of the cross-links.

Figure 7:
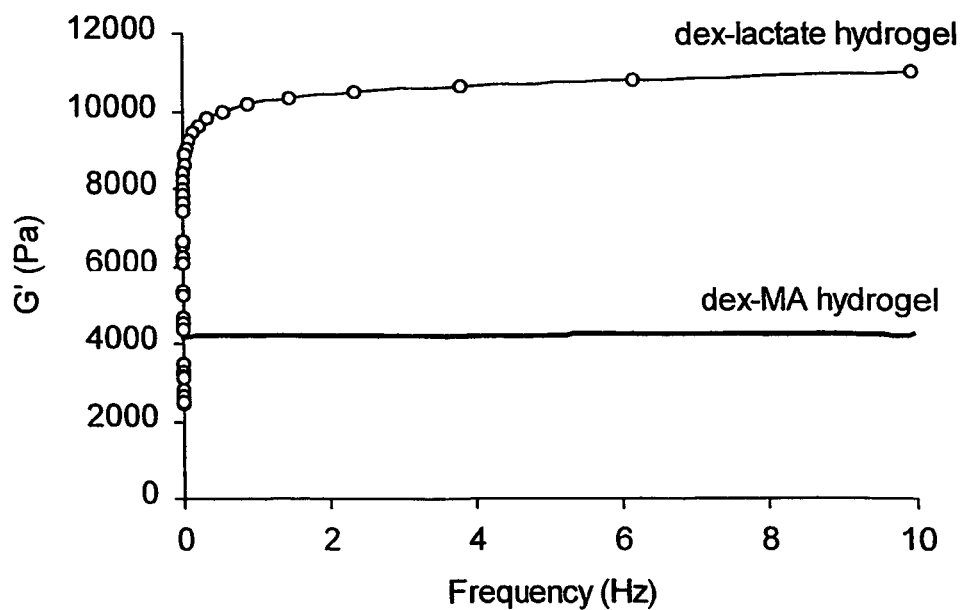

Elastic properties as function of the frequency. FIG. 7 compares a G' profile of a dex-lactate hydrogel and a chemically cross-linked methacrylated-dextran hydrogel, respectively, as a function of the frequency. G' of the dex-methacrylate hydrogel was independent of the applied frequency again indicating the existence of a real rubbery network, which is expected in hydrogels with permanent (chemical) cross-links. (See for example De Smedt, S. C.; Lauwers, A.; Demeester, J.; Van Steenbergen, M. J.; Hennink, W. E.; Roefs, S. P. F. M. *Micromolecules* 1995, 28, 5082-5088). However, G' of the dex-lactate gel decreased considerably with decreasing frequency. This again demonstrates the physical, i.e. reversible (transient) nature of the cross-links (FIG. 7). At low frequencies the cross-links break and re-form at long time scales (the network relaxation process), whereas at high frequencies the time scale becomes smaller and the cross-links act as if permanent, resulting in increasing G'.

Figure 8A:
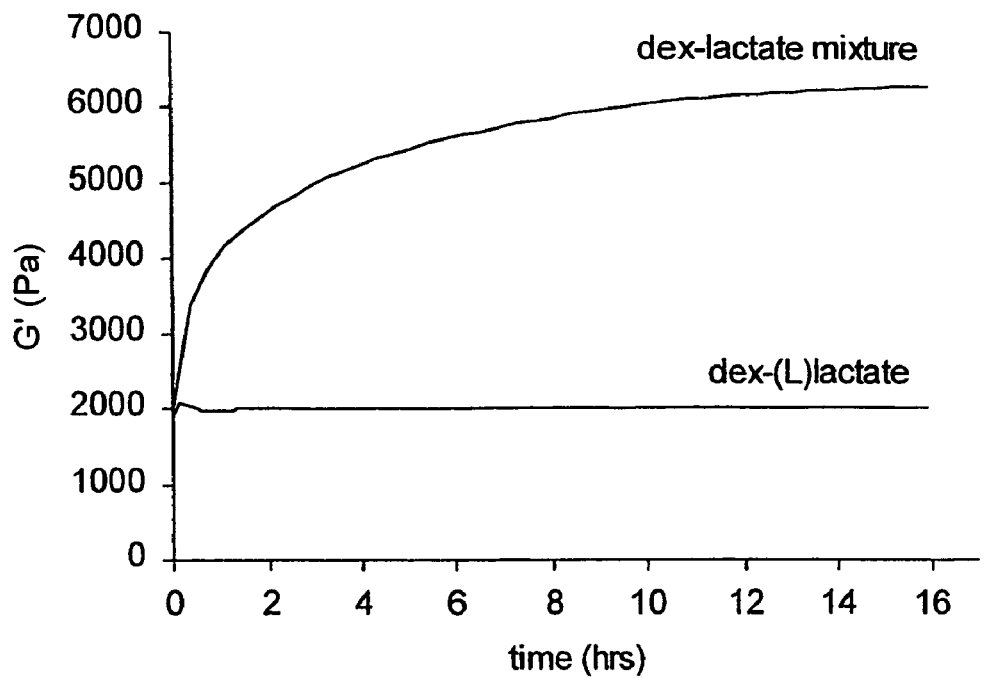
Figure 8B:
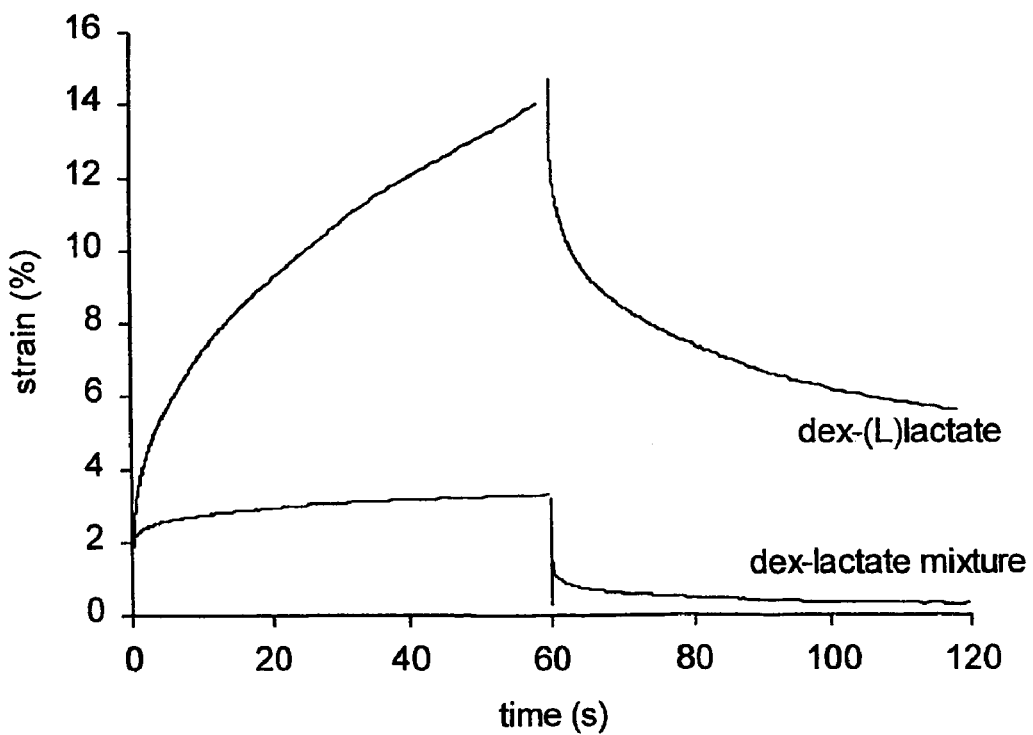

Influence of DP, DS and water content on gel formation. The G' profiles shown in FIG. 4 were obtained using a dex-lactate sample with $DP_{av}$ 9 and DS 3. When dex-lactates with a higher DP and higher DS were used, the dex-(L)lactate (or dex-(D)lactate) solutions showed visco-elastic behavior. This is probably caused by the association of the longer lactic acid chains with oligomers of the same chirality, which also results in a poorer water solubility. However, in this sample gelation as function of the time was not observed. In contrast, the dex-lactate mixture clearly gelled as observed from an increase in G' (FIG. 8A). The formation of a gel was confirmed by creep experiments: the dex-lactate mixture showed an almost elastic behavior, whereas the dex-(L)lactate system is typical visco-elastic material (FIG. 8B).

Figure 9A:
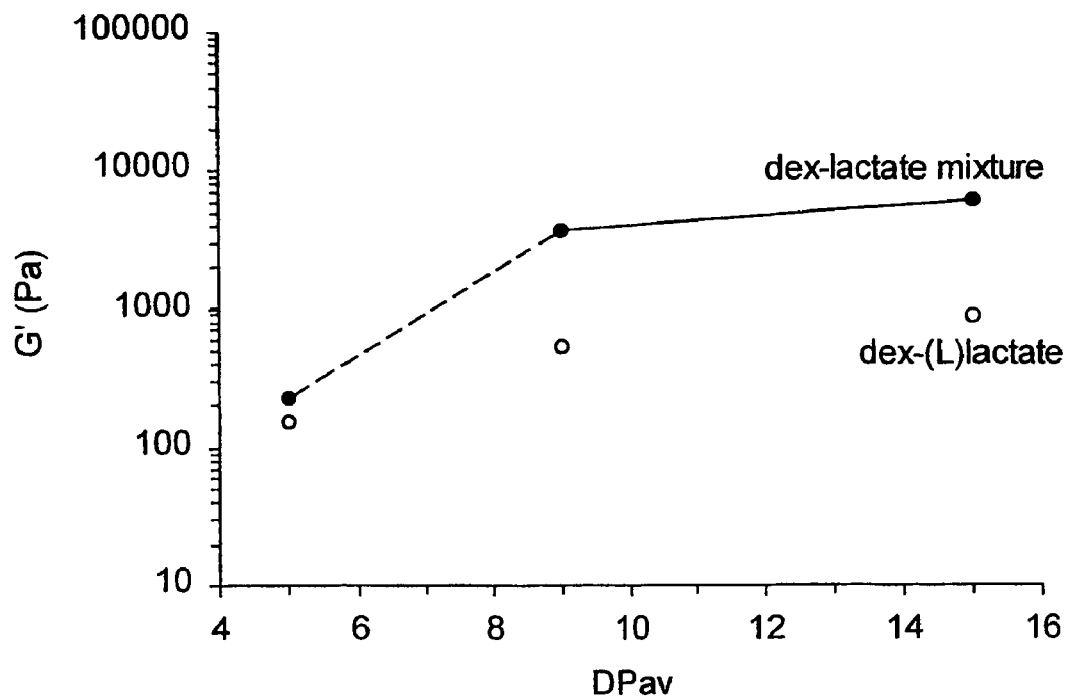
Figure 9B:
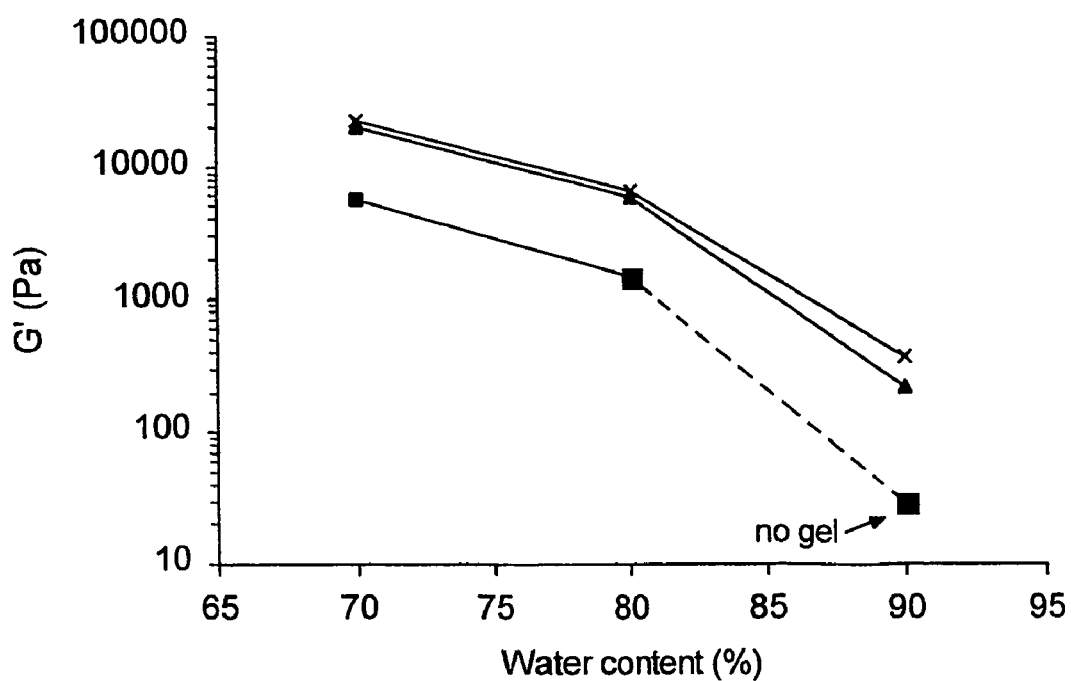

FIG. 9 shows the influence of the degree of polymerization (A), the water content and the degree of substitution (B) on G', 18 hours after mixing the dex-(L)lactate with the dex-(D) lactate solution. Mixing dex-(L)lactate $DP_{av}$ 5 with dex-(D) lactate $DP_{av}$ 5 solution resulted in a slight increase in G' compared with the G' value of the corresponding dex-(L) lactate system. This indicates that a weak hydrogel was formed, as a result of the fact that the oligomers did not have sufficient length to associate with each other. Mixing of dex-lactates with higher degrees of polymerization resulted in formation of a gel as reflected by a substantially greater value for G' of the mixture compared to the G' for one of the isomers (compare open and closed symbols, FIG. 9A). As FIG. 9B shows, stronger gels were obtained by increasing the degree of substitution and by decreasing the water content of the system.

Monodisperse Lactic Acid Oligomers Grafted to Dextran

Rheology. Monodisperse lactic acid oligomers, with a degree of polymerization ranging from 8 to 12, were coupled to dextran to determine the effect of the lactic acid chain length on the gel formation. Mixtures of dex-(L)lactate and dex-(D)lactate with the same degree of polymerization of the lactic acid oligomers were investigated for their ability to form a gel (Table 4). From these data it can be seen that mixtures of dex-(L)lactate and dex-(D)lactate with a DP lower than 11 are mainly viscous, even when a high degree of substitution (DS 17) or low water content (70%) was used. On the other hand, for dex-lactate DP 11 or 12, an increase in G' was observed after mixing the dex-(L)lactate and dex-(D)lactate product, and a hydrogel was formed. Gel formation was confirmed by a creep experiment, which showed almost elastic behavior of the mixture. A gel was also obtained with dex-(L)lactate DP 12 and DS 17.

TABLE 4

Rheology and PAS data of the mixture of monodisperse dex- (L) lactate and dex- (D) lactate.

| DP | DS | % water | Rheology Creep | Gelation | PAS Stereocomplex |
|----|----|---------|----------------|----------|-------------------|
| 8  | 17 | 70      | V              | –        | –                 |
| 8  | 17 | 80      | V              | –        | –                 |
| 10 | 6  | 70      | V              | –        | +/–               |
| 10 | 6  | 80      | V              | –        | –                 |
| 10 | 15 | 70      | V              | –        | +                 |
| 10 | 15 | 80      | V              | –        | –                 |
| 11 | 17 | 80      | E              | +        | + +               |
| 12 | 8  | 80      | E              | +        | + +               |

V = mainly viscous, E = mainly elastic

Figure 10:
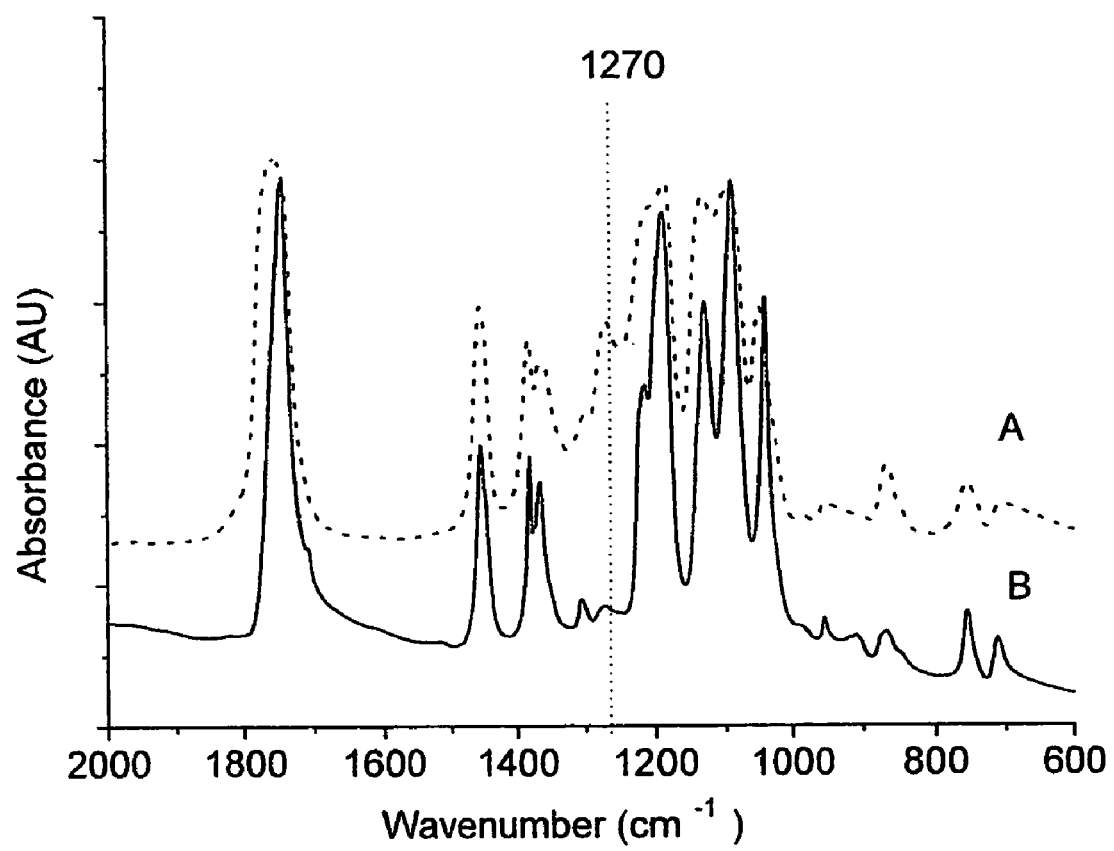

FTIR transmission and photoacoustic spectrometry. Infrared spectroscopy was applied to investigate the possible stereocomplex formation in the monodisperse dex-lactate gels. It was shown by Vert et al. (Kister, G.; Cassanas, G.; Vert, M. *Polymer* 1995, 39, 267-273) that IR spectroscopy can be used to distinguish between $10_3$ and $3_1$ helical conformations of the crystalline homopolymer of poly(lactide) (PLA) and the PLA stereocomplex, respectively. Since sharp IR-band shapes were observed for the monodisperse products, they were used for interpretation purposes. FTIR-transmission spectra of the free monodisperse lactic acid oligomer (DP 8) and its corresponding blend, which form stereocomplexes upon mixing, were recorded (FIG. 10). In the stereocomplex the most pronounced difference was the disappearance of the absorption peak at 1270 cm$^{-1}$ ($\delta CH_3$, $\nu COC$, indicated by the dotted line).

Figure 11A:
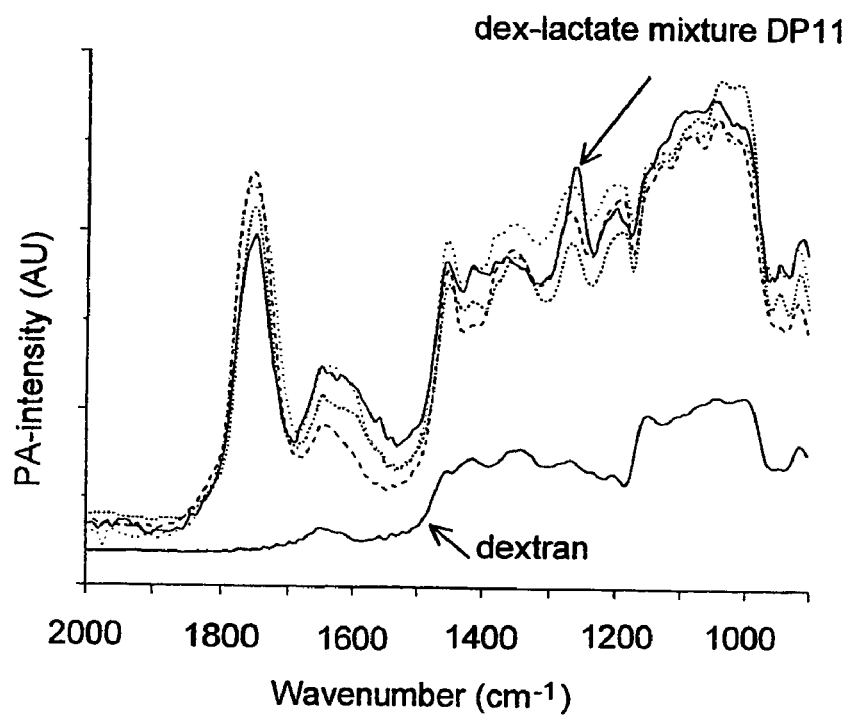
Figure 11B:
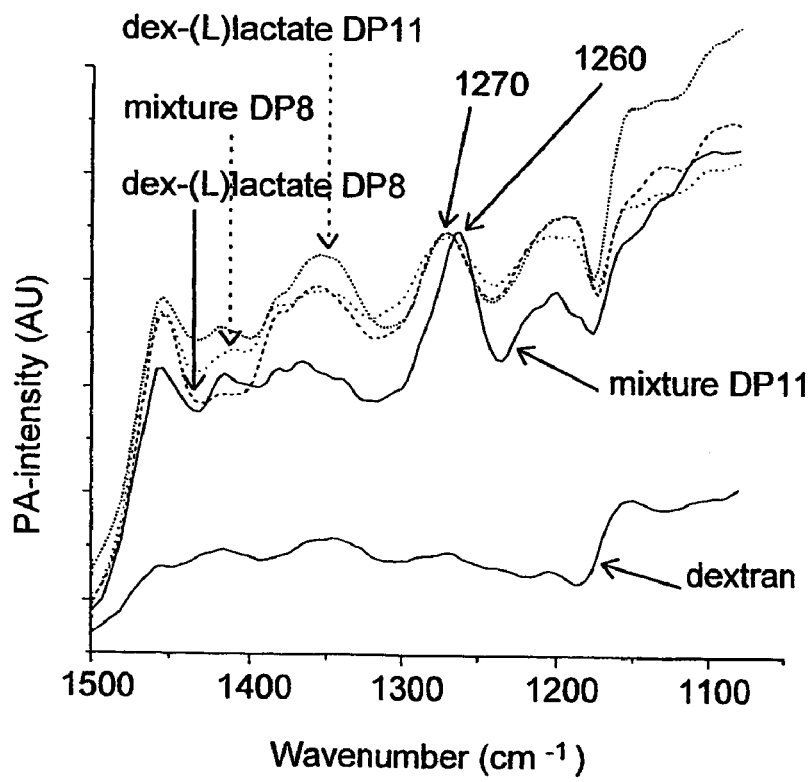

After rheology measurement, the dex-(monodisperse)lactate products were dried at ambient temperature. Next, IR spectra of these dried products were recorded with the PA-detection method, which turned out to be qualitatively comparable to FTIR-transmission method. FIG. 11 shows that similar IR spectra were obtained for the dex-(L)lactate with DP 8 and DP 11, as well as for the dex-lactate mixture with DP 8, in which less or no gelation occurred (Table 4). Interestingly, for the dex-lactate mixture with DP 11 (rheology experiments demonstrated the formation of a gel, Table 4) some clear IR-frequency shifts were observed in the IR spectrum. The observed shift from 1270 to 1260 cm$^{-1}$ (FIG. 11B) can likely be ascribed to the formation of stereocomplexes in the dex-lactate mixture. In Table 4 the presence of stereocomplexes, as detected by IR-PA, in different dex-lactate mixtures is given. For systems with DP 11 and 12, gelation (based on rheology) was clearly associated with the presence of stereocomplexes.

The dex-lactate mixtures with DP 10 (DS6 and DS15) and a water content of 70% showed the same IR-frequency shift (from 1270 to 1260 cm$^{-1}$) as well, although for these mixtures the rheology data indicated mainly viscous behavior. This indicates that stereocomplexes are formed in the dex-lactate mixture with DP 10 and a water content of 70%. However, only a few physical interactions (stereocomplexes) may be present, which are not sufficient to form an completely elastic network. For the free lactic acid oligomers a minimum DP of 7 is required for the stereocomplexation. For dex-lactates longer lactic acid chains are required to obtain the parallel orientation of at least 7 lactic acid units of opposite chirality needed for the formation of stereocomplexes.

EXAMPLE 5

Protein Release from Dextran Gels Crosslinked by Stereocomplex Formation

Gels with an initial water content of 80% were prepared as follows. Around 400 mg (accurately weighed) of dex-L-lactate (DP$_{av}$ 9, DS 12) was added to 1.6 ml of an aqueous solution of lysozyme or IgG (30 mg/ml in 100 mM phosphate buffer pH 7.2). The lysozyme and IgG were used as model active ingredients. In another vial, 400 mg of dex-D-lactate (Dp$_{av}$ 9, DS 14) was added to 1.6 ml of an aqueous solution of lysozyme or IgG (30 mg/ml in 100 mM phosphate buffer pH 7.2). The modified dextran were allowed to solubilize for 48 hours at 4° C. Thereafter 900 mg of both solutions were mixed well and allowed to gelatinize in a plastic tube (diameter 1.0 cm, length 2.0 cm) for 72 hours at 4° C.

Gels with an initial water content of 60% were prepared by adjusting the amount of dex-lactate MEE added to the protein solution. The gels were removed from the plastic tubes, weighed, added to 20 ml of an aqueous solution of phosphate buffer (100 mM, pH 7.2) and incubated at 37° C. At regular time points, sample of 2 ml were withdrawn and replaced by fresh buffer.

Figure 12A:
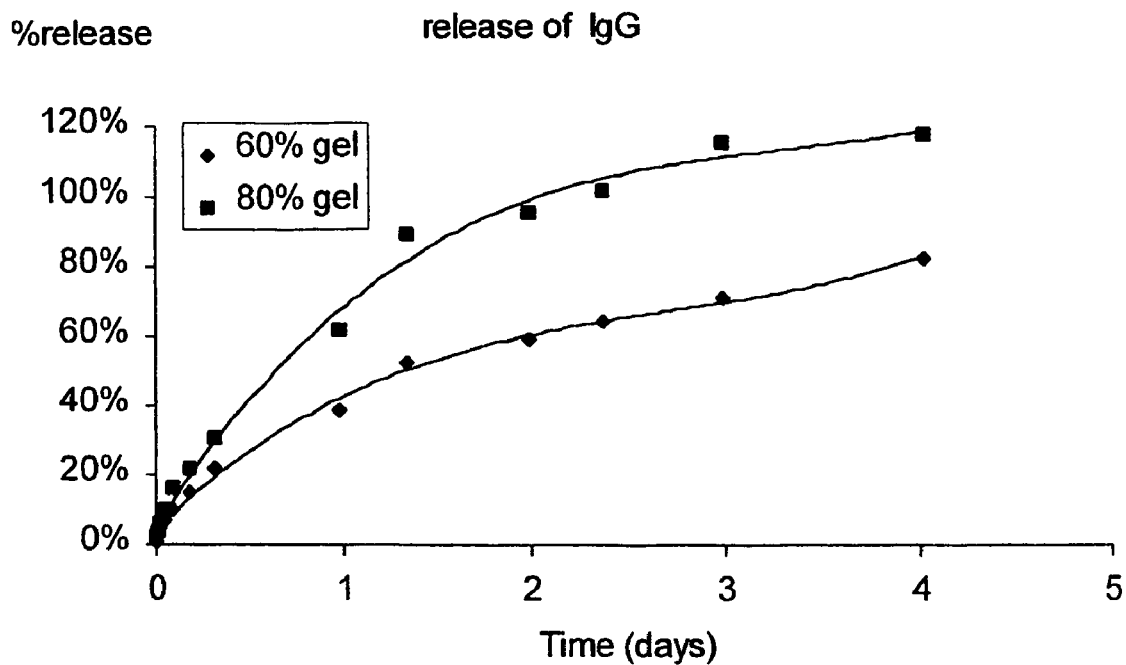
Figure 12B:
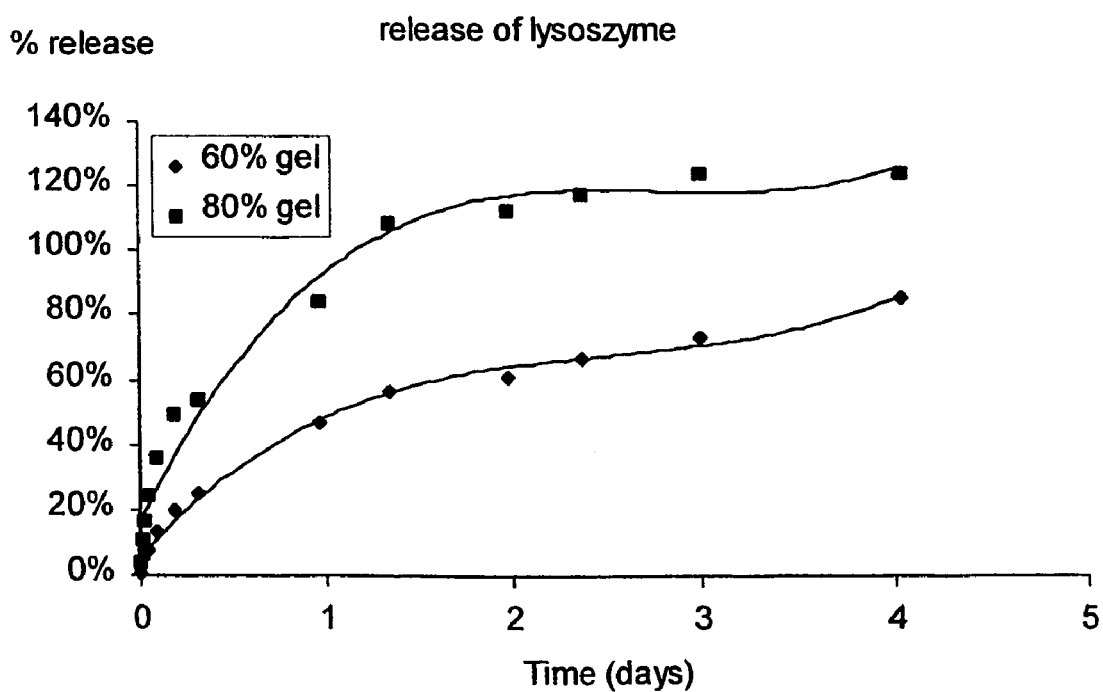

The protein concentration in the different samples was determined by the BCA-assay (K. Smith, R. I. Krohn, G. T. Hermanson, A. K. Mallia, F. H. Provenza, E. K. Fujimoto, N. M. Goeke, B. J. Olson, D. C. Klenk Anal. Biochem., vol. 150, p. 76-85, 1985) and used to calculate the cumulative amount of protein released. FIGS. 12A and 12B show the results.

From these results it follows that the release is dependent on the hydrodynamic size of the protein and the initial water content of the gel.

EXAMPLE 6

Synthesis of Lactate Oligomer with Terminal Free Carboxylic Acid Groups

In the stereocomplex of poly(L-lactide) and poly(D-lactide), a poly(L-lactide) segment and poly(D-lactide) segment are packed in parallel fashion (Okihara, T.; Tsuji, M.; Kawaguchi, A.; Katayama, K. I.; Tsuji, H.; Hyon, S. H.; Ikada, Y. *J. Macromol. Sci. Phys.* 1991, B30(1&2), 119-140). It was studied whether stereocomplex formation between of oligomers grafted to dextrans was enhance once one of the oligomers is coupled via its terminal hydroxyl group to dextran and the other via caboxylic acid. To this end one oligomer was coupled via its terminal hydroxyl group to dextran and the oligomer of opposite chirality via its carboxylic acid group.

A lactate acid oligomer with a terminal carboxylic acid group was synthesized as follows. A mixture of L-lactide (5 g, 35 mmol) and benzyl alcohol (0.85 g, 7.8 mmol) was heated to 120° C. Stannous octoate (tin(II) bis(2-ethylhexanoate), SnOct$_2$, 70 mg, 0.17 mmol) was added and the mixture was stirred at 120° C. for 2 hr. To protect the terminal hydroxyl group, acetic anhydride (0.875 g, 8.6 mmol) was added and the heating was continued for 3 hr. The formed acetic acid and the excess of acetic anhydride was removed by applying vacuum before cooling down the reaction mixture. A viscous clear paste was obtained in a quantitative yield. $^1$H NMR (CDCl$_3$): $\delta$ (ppm) 7.34 (m, 5H, ArH), 5.02-5.23 (m, 11H, CH—OC=O) and ArCH$_2$O), 2.12 (s, 3H, CH$_3$=O), 1.47-1.62 (m, 27H, CH$_3$ lactate).

The obtained benzyl-lactate$_9$acetate was dissolved in 30 ml ethyl acetate. Nitrogen was bubbled through the solution and 30 mg of Pd/C was added. The mixture was connected a balloon filled with hydrogen and stirred for 24 hr at room temperature. The mixture was filtered over celite and the solvent was removed by rotary evaporation. The last traces of ethyl acetate were removed under high vacuum. A viscous clear liquid was obtained in quantitative yield α-carboxyl lactate$_9$acetate) $^1$H NMR (CDCl$_3$): $\delta$ (ppm) 7.34 (m, 5H, ArH), 5.02-5.23 (m, 11H, CH—OC=O) and ArCH$_2$O), 2.12 (s, 3H, CH$_3$=O), 1.47-1.68 (m, 27H, CH$_3$ lactate).

Synthesis of dextran-(lactate$_9$) acetate. Glassware was dried in an oven at 150° C. for at least one hour. Dextran was dried in a vacuum oven at 40° C. A hot 10 ml flask was loaded with 100 mg LiCl and evacuated to dry the salt. After cooling to room temperature, 535 mg dry dextran 40.000 was added and the flask was evacuated three times and filled with nitrogen. The flask was then closed with a septum and 5 ml dry DMF was added with a dry syringe. The mixture was heated to 100° C. to dissolve the dextran and then cooled to room temperature.

Another dry 10 ml flask was loaded with α-carboxyl lactate$_9$ acetate (235 mg, 0.33 mmol), 4(dimethylamino)-pyridinium-4-toluene sulfonate (16 mg, 0.05 mmol) and dicyclohexyl carbodiimide (100 mg, 0.50 mmol). The flask was evacuated three times and filled with nitrogen, while slightly warming the flask with a hairdryer. The flask was then closed with a septum and the dextran solution was transferred into the flask with the help of a needle. The mixture was stirred at room temperature for 24 h.

The reaction mixture was diluted with 20 ml water and dialysed against water (5 L) at 4° C. during one night. The product was freeze dried, and then stirred with 50 ml $CH_2Cl_2$ for one hour, filtered and dried in vacuum.

Yield: 82% of a white powder. The DS was 9.7 (NMR-analysis). Products with other degree of substitutions were synthesized by adjusting the ratio dextran/oligomer.

Rheological Evaluation. For the rheological experiments two types of polymer solutions were prepared: one contains dex-(L)lactate and the other dex-(D)lactate. The dissolution time was at least one day at room temperature. Acetate buffer pH 4 was selected as solvent to prevent hydrolysis of the dex-lactate.

Equal amounts of the dex-(L)lactate and the dex-(D)lactate solutions were mixed, homogenized and quickly applied on the rheometer (AR 100 instrument of TA Instruments, Gent, Belgium). A cone-plate measuring geometry (steel, 2 cm diameter with an angle of 1 degree; gap 31 μm) was used when only a small amount of material was available. Gelation of the dex-lactate solutions took place between the cone and plate of the measuring geometry. A solvent trap was used to prevent evaporation of the solvent. In addition, a thin layer of silicon oil (110 mPa·s) was applied to surround the dex-lactate sample thereby preventing evaporation.

Gelation of the mixture of dex-lactate solutions was monitored by measuring the shear storage modulus (G'), as well as the loss modulus (G") at 20° C. for 18 hours. A frequency of 1 Hz and a controlled strain of 1% were applied. The strain used in these experiments was as low as possible to minimize the influence of deformation on the formation of the dex-lactate hydrogels. The rheological characteristics of two systems were compared.

In system I both the L-lactic acid oligomer and the D-lactic acid oligomer are coupled to dextran via their terminal hydroxyl groups (dex-lactate-MEE) essentially as described in Example 1-4. In System II the L-lactic acid oligomer is coupled via its terminal carboxylic group (dex-lactate-acetate) as described in the present Example above. The D-oligomer was coupled via its terminal hydroxyl group (dex-lactate-MEE) essentially as described in Example 1-4.

TABLE 5 summarizes the results.

| System, % $H_2O$ | L-Oligomer graft* | D-oligomer graft* | G'(Pa) | tan δ |
|---|---|---|---|---|
| I, 70% | L-lactate-MEE, DS 3 | D-lactate-MEE, DS 4 | 5749 | 0.11 |
| II, 70% | L-lactate-Ac, DS 4 | D-lactate-MEE, DS 4 | 7806 | 0.16 |
| I, 80% | L-lactate-MEE, DS 12 | D-lactate-MEE, DS 14 | 5807 | 0.17 |
| II, 80% | L-lactate-Ac, DS 10 | D-lactate-MEE, DS 14 | 17240 | 0.14 |
| I, 70% | L-lactate-MEE, DS 12 | D-lactate-MEE, DS 14 | 20040 | 0.14 |
| II, 70% | L-lactate-Ac, DS 10 | D-lactate-MEE, DS 14 | 30860 | 0.11 |

*$DP_{av}$= 9, **after 18 hours

Table 5 clearly shows that by coupling of oligomer via its hydroxyl group and the other oligomer of opposite chirality via its carboxylic acid group, stronger gels were obtained in comparison with gels in which both oligomers were coupled via their hydroxyl groups (compare G' values for system II with those of the corresponding gels for system I).

It is therefore advantageous to couple one oligomer via its terminal hydroxyl group to dextran and the oligomer of opposite chirality via its carboxylic acid group.

The invention claimed is:

1. Hydrogel composition comprised of a mixture of
   (A) a dextran polymer grafted with homo-oligomers of L-lactic acid, and
   (B) a dextran polymer grafted with homo-oligomers of D-lactic acid,
   in an aqueous system,
   wherein said homo-oligomers of L-lactic acid and said homo-oligomers of D-lactic acid have 7-25 lactic acid monomers on average.

2. Hydrogel composition according to claim 1, wherein the hydrogel is formed in microspheres.

3. Hydrogel composition according to claim 1, further comprising an active ingredient.

4. Hydrogel composition according to claim 3, wherein the active ingredient is a drug to be released.

5. A method for drug delivery comprising administering the hydrogel composition of claim 4.

6. Process for the preparation of a hydrogel comprising:
   a) polymerizing L-lactic acid, optionally in the presence of a suitable initiator;
   b) polymerizing D-lactic acid, optionally in the presence of a suitable initiator;
   c) reacting the product of step a) with a suitable coupling compound and a dextran polymer to form a dextran polymer grafted with homo-oligomers of L-lactic acid;
   d) reacting the product of step b) with a suitable coupling compound and a dextran polymer to form a dextran polymer grafted with homo-oligomers of D-lactic acid;
   wherein said homo-oligomers of L-lactic acid and said homo-oligomers of D-lactic acid have 7-25 lactic acid monomers on average; and
   e) mixing the product of step c) and the product of step d) in an aqueous system to provide said hydrogel.

7. Process according to claim 6, said suitable initiator comprising a primary or secondary hydroxyl group.

8. Process according to claim 6, wherein an active ingredient is added prior to or during step e).

9. Process according to claim 8, wherein the active ingredient is a drug to be released.

10. Process according to claim 9, wherein the drug to be released is selected from proteins and proteinaceous products.

* * * * *